(12) United States Patent
Roorda et al.

(10) Patent No.: US 8,657,852 B2
(45) Date of Patent: Feb. 25, 2014

(54) CLOSURE DEVICE

(71) Applicant: Abbott Vascular Inc., Santa Clara, CA (US)

(72) Inventors: Wouter E. Roorda, Palo Alto, CA (US); Kelly J. McCrystle, Menlo Park, CA (US); Ian J. Clark, West Bloomfield, CA (US); Laveille K. Voss, Belmont, CA (US); Ni Ding, San Jose, CA (US)

(73) Assignee: Abbott Vascular Inc., Santa Clara, CA (US)

( * ) Notice: Subject to any disclaimer, the term of this patent is extended or adjusted under 35 U.S.C. 154(b) by 0 days.

(21) Appl. No.: 13/791,829

(22) Filed: Mar. 8, 2013

(65) Prior Publication Data

US 2013/0190810 A1 Jul. 25, 2013

Related U.S. Application Data

(63) Continuation of application No. 12/608,769, filed on Oct. 29, 2009.

(60) Provisional application No. 61/109,822, filed on Oct. 30, 2008, provisional application No. 61/143,748, filed on Jan. 9, 2009.

(51) Int. Cl.
*A61B 17/08* (2006.01)

(52) U.S. Cl.
USPC .......................................... 606/213; 606/214

(58) Field of Classification Search
None
See application file for complete search history.

(56) References Cited

U.S. PATENT DOCUMENTS

| 287,046 | A | 10/1883 | Norton |
| 438,400 | A | 10/1890 | Brennen |
| 556,082 | A | 3/1896 | Boeddinghaus |
| 1,088,393 | A | 2/1914 | Backus |
| 1,242,139 | A | 10/1917 | Callahan |
| 1,331,401 | A | 2/1920 | Summers |
| 1,480,935 | A | 1/1924 | Gleason |
| 1,596,004 | A | 8/1926 | De Bengoa |
| 1,647,958 | A | 11/1927 | Ciarlante |
| 1,880,569 | A | 10/1932 | Weis |

(Continued)

FOREIGN PATENT DOCUMENTS

| AU | 2003297432 | 7/2004 |
| CA | 2 339 060 | 2/2000 |

(Continued)

OTHER PUBLICATIONS

U.S. Appl. No. 11/344,891, Mail Date May 15, 2013, Issue Notification.

(Continued)

*Primary Examiner* — Corrine M McDermott
*Assistant Examiner* — Son Dang
(74) *Attorney, Agent, or Firm* — Workman Nydegger; Randy Shen

(57) ABSTRACT

A device for closing an opening in a wall of a body lumen includes a closure element with a first flange and a second flange. Both the first flange and the second flange may have a delivery cross-sectional dimension and a deployed cross-sectional dimension. The device for closing an opening further includes a first coupler element disposed on the first flange and a second coupler element disposed on the second flange, the first and second coupler elements cooperating to couple the first flange to the second flange.

14 Claims, 3 Drawing Sheets

(56) References Cited

U.S. PATENT DOCUMENTS

| | | |
|---|---|---|
| 2,087,074 A | 7/1937 | Tucker |
| 2,210,061 A | 8/1940 | Caminez |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,684,070 A | 7/1954 | Kelsey |
| 2,755,699 A | 7/1956 | Forster |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,348,595 A | 10/1967 | Stevens, Jr. |
| 3,357,070 A | 12/1967 | Sloan |
| 3,482,428 A | 12/1969 | Kapitanov et al. |
| 3,494,533 A | 2/1970 | Green et al. |
| 3,510,923 A | 5/1970 | Blake |
| 3,523,351 A | 8/1970 | Filia |
| 3,586,002 A | 6/1971 | Wood et al. |
| 3,604,425 A | 9/1971 | Le Roy |
| 3,618,447 A | 11/1971 | Goins |
| 3,677,243 A | 7/1972 | Nerz |
| 3,682,180 A | 8/1972 | McFarlane |
| 3,757,629 A | 9/1973 | Schneider |
| 3,805,337 A | 4/1974 | Branstetter |
| 3,823,719 A | 7/1974 | Cummings |
| 3,828,791 A | 8/1974 | Santos |
| 3,856,016 A | 12/1974 | Davis |
| 3,874,388 A * | 4/1975 | King et al. ............... 606/232 |
| 3,908,662 A | 9/1975 | Razgulov et al. |
| 3,926,194 A | 12/1975 | Greenberg et al. |
| 3,939,820 A | 2/1976 | Grayzel |
| 3,944,114 A | 3/1976 | Coppens |
| 3,960,147 A | 6/1976 | Murray |
| 3,985,138 A | 10/1976 | Jarvik |
| 4,007,743 A | 2/1977 | Blake |
| 4,014,492 A | 3/1977 | Rothfuss |
| 4,018,228 A | 4/1977 | Goosen |
| 4,047,533 A | 9/1977 | Perciaccante et al. |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,189,808 A | 2/1980 | Brown |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,267,995 A | 5/1981 | McMillan |
| 4,273,129 A | 6/1981 | Boebel |
| 4,274,415 A | 6/1981 | Kanamoto et al. |
| 4,278,091 A | 7/1981 | Borzone |
| 4,317,445 A | 3/1982 | Robinson |
| 4,317,451 A | 3/1982 | Cerwin et al. |
| 4,318,401 A | 3/1982 | Zimmerman |
| 4,327,485 A | 5/1982 | Rix |
| 4,345,606 A | 8/1982 | Littleford |
| 4,359,052 A | 11/1982 | Staub |
| 4,368,736 A | 1/1983 | Kaster |
| 4,396,139 A | 8/1983 | Hall et al. |
| 4,407,286 A | 10/1983 | Noiles et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Vailancourt |
| 4,526,174 A | 7/1985 | Froehlich |
| 4,586,503 A | 5/1986 | Kirsch et al. |
| 4,592,498 A | 6/1986 | Braun et al. |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,651,737 A | 3/1987 | Deniega |
| 4,664,305 A | 5/1987 | Blake, III et al. |
| 4,665,906 A | 5/1987 | Jervis |
| 4,687,469 A | 8/1987 | Osypka |
| 4,693,249 A | 9/1987 | Schenck et al. |
| 4,697,312 A | 10/1987 | Freyer |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,885,003 A | 12/1989 | Hillstead |
| 4,886,067 A | 12/1989 | Palermo |
| 4,887,601 A | 12/1989 | Richards |
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,967,949 A | 11/1990 | Sandhaus |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,035,692 A | 7/1991 | Lyon et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |

(56) References Cited

U.S. PATENT DOCUMENTS

| | | |
|---|---|---|
| 5,122,122 A | 6/1992 | Allgood |
| 5,122,156 A | 6/1992 | Granger et al. |
| 5,131,379 A | 7/1992 | Sewell, Jr. |
| 5,141,520 A | 8/1992 | Goble et al. |
| 5,147,381 A | 9/1992 | Heimerl et al. |
| 5,156,609 A | 10/1992 | Nakao et al. |
| 5,163,343 A | 11/1992 | Gish |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,176,648 A | 1/1993 | Holmes et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,193,533 A | 3/1993 | Body et al. |
| 5,197,971 A | 3/1993 | Bonutti |
| 5,207,697 A | 5/1993 | Carusillo et al. |
| 5,209,756 A | 5/1993 | Seedhorm et al. |
| 5,217,024 A | 6/1993 | Dorsey et al. |
| 5,222,974 A | 6/1993 | Kensey et al. |
| 5,226,908 A | 7/1993 | Yoon |
| 5,236,435 A | 8/1993 | Sewell, Jr. |
| 5,242,456 A | 9/1993 | Nash et al. |
| 5,242,457 A | 9/1993 | Akopov et al. |
| 5,242,459 A | 9/1993 | Buelna |
| 5,243,857 A | 9/1993 | Janota |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A | 4/1994 | Gourlay et al. |
| 5,304,184 A | 4/1994 | Hathaway et al. |
| 5,304,204 A | 4/1994 | Bregen |
| 5,306,254 A | 4/1994 | Nash et al. |
| 5,309,927 A | 5/1994 | Welch |
| 5,318,542 A | 6/1994 | Hirsch et al. |
| 5,320,639 A | 6/1994 | Rudnick |
| 5,327,908 A | 7/1994 | Gerry |
| 5,330,445 A | 7/1994 | Haaga |
| 5,330,503 A | 7/1994 | Yoon |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher et al. |
| 5,352,229 A | 10/1994 | Goble et al. |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,383,896 A | 1/1995 | Gershony et al. |
| RE34,866 E | 2/1995 | Kensey et al. |
| 5,392,978 A | 2/1995 | Valez et al. |
| 5,395,030 A | 3/1995 | Kuramoto et al. |
| 5,404,621 A | 4/1995 | Heinke |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,765 A | 5/1995 | Weldon et al. |
| 5,419,777 A | 5/1995 | Hofling |
| 5,421,832 A | 6/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,451,235 A | 9/1995 | Lock et al. |
| 5,456,400 A | 10/1995 | Shichman et al. |
| 5,462,561 A | 10/1995 | Voda |
| 5,464,413 A | 11/1995 | Siska, Jr. et al. |
| 5,466,241 A | 11/1995 | Leroy et al. |
| 5,470,010 A | 11/1995 | Rothfuss et al. |
| 5,471,982 A | 12/1995 | Edwards et al. |
| 5,474,557 A | 12/1995 | Mai |
| 5,474,569 A | 12/1995 | Zinreich et al. |
| 5,476,505 A | 12/1995 | Limon |
| 5,478,352 A | 12/1995 | Fowler |
| 5,478,353 A | 12/1995 | Yoon |
| 5,478,354 A | 12/1995 | Tovey et al. |
| 5,486,195 A | 1/1996 | Myers et al. |
| 5,497,933 A | 3/1996 | DeFonzo et al. |
| 5,507,744 A | 4/1996 | Tay et al. |
| 5,507,755 A | 4/1996 | Gresl et al. |
| 5,522,840 A | 6/1996 | Krajicek |
| 5,527,322 A | 6/1996 | Klein et al. |
| 5,536,251 A | 7/1996 | Evard et al. |
| 5,540,712 A | 7/1996 | Kleshinski et al. |
| 5,540,716 A | 7/1996 | Hlavacek |
| 5,544,802 A | 8/1996 | Crainich |
| 5,547,474 A | 8/1996 | Kloeckl et al. |
| 5,560,532 A | 10/1996 | DeFonzo et al. |
| 5,571,120 A | 11/1996 | Yoon |
| 5,573,784 A | 11/1996 | Badylak et al. |
| 5,575,771 A | 11/1996 | Walinsky |
| 5,582,616 A | 12/1996 | Bolduc et al. |
| 5,584,879 A | 12/1996 | Reimold et al. |
| 5,591,205 A | 1/1997 | Fowler |
| 5,593,412 A | 1/1997 | Martinez et al. |
| 5,601,602 A | 2/1997 | Fowler |
| 5,609,597 A | 3/1997 | Lehrer |
| 5,613,974 A | 3/1997 | Andreas et al. |
| 5,618,291 A | 4/1997 | Thompson et al. |
| 5,620,452 A | 4/1997 | Yoon |
| 5,620,461 A | 4/1997 | Muijs et al. |
| 5,626,614 A | 5/1997 | Hart |
| 5,634,936 A | 6/1997 | Linden et al. |
| 5,643,318 A | 7/1997 | Tsukernik et al. |
| 5,645,565 A | 7/1997 | Rudd et al. |
| 5,645,566 A | 7/1997 | Brenneman et al. |
| 5,645,567 A | 7/1997 | Crainich |
| 5,649,959 A | 7/1997 | Hannam et al. |
| D383,539 S | 9/1997 | Croley |
| 5,669,935 A | 9/1997 | Rosenman et al. |
| 5,674,231 A | 10/1997 | Green et al. |
| 5,676,689 A | 10/1997 | Kensey et al. |
| 5,676,974 A | 10/1997 | Valdes et al. |
| 5,681,280 A | 10/1997 | Rusk et al. |
| 5,681,334 A | 10/1997 | Evans et al. |
| 5,683,405 A | 11/1997 | Yacoubian et al. |
| 5,690,674 A | 11/1997 | Diaz |
| 5,695,504 A | 12/1997 | Gifford, III et al. |
| 5,695,505 A | 12/1997 | Yoon |
| 5,695,524 A | 12/1997 | Kelley et al. |
| 5,700,273 A | 12/1997 | Buelna et al. |
| 5,709,224 A | 1/1998 | Behl et al. |
| 5,715,987 A | 2/1998 | Kelley et al. |
| 5,716,375 A | 2/1998 | Fowler |
| 5,720,755 A | 2/1998 | Dakov |
| 5,725,498 A | 3/1998 | Janzen et al. |

(56) References Cited

U.S. PATENT DOCUMENTS

| | | |
|---|---|---|
| 5,725,552 A | 3/1998 | Kotula et al. |
| 5,725,554 A | 3/1998 | Simon et al. |
| 5,728,110 A | 3/1998 | Vidal et al. |
| 5,728,114 A | 3/1998 | Evans et al. |
| 5,728,116 A | 3/1998 | Rosenman |
| 5,728,122 A | 3/1998 | Leschinsky et al. |
| 5,728,132 A | 3/1998 | Van Tassel et al. |
| 5,728,133 A | 3/1998 | Kontos |
| 5,732,872 A | 3/1998 | Bolduc et al. |
| 5,735,736 A | 4/1998 | Volk |
| 5,735,873 A | 4/1998 | MacLean |
| 5,749,826 A | 5/1998 | Faulkner |
| 5,752,966 A | 5/1998 | Chang |
| 5,755,726 A | 5/1998 | Pratt et al. |
| 5,755,778 A | 5/1998 | Kleshinski |
| 5,766,217 A | 6/1998 | Christy |
| 5,766,246 A | 6/1998 | Mulhauser et al. |
| 5,769,870 A | 6/1998 | Salahieh et al. |
| 5,776,147 A | 7/1998 | Dolendo |
| 5,779,707 A | 7/1998 | Bertholet et al. |
| 5,780,807 A | 7/1998 | Saunders |
| 5,782,844 A | 7/1998 | Yoon et al. |
| 5,782,860 A | 7/1998 | Epstein et al. |
| 5,782,861 A | 7/1998 | Cragg et al. |
| 5,795,958 A | 8/1998 | Rao et al. |
| 5,797,928 A | 8/1998 | Kogasaka |
| 5,797,931 A | 8/1998 | Bito et al. |
| 5,797,933 A | 8/1998 | Snow et al. |
| 5,797,958 A | 8/1998 | Yoon |
| 5,797,960 A | 8/1998 | Stevens et al. |
| 5,810,776 A | 9/1998 | Bacich et al. |
| 5,810,846 A | 9/1998 | Virnich et al. |
| 5,810,851 A | 9/1998 | Yoon |
| 5,817,113 A | 10/1998 | Gifford, III et al. |
| 5,820,631 A | 10/1998 | Nobles |
| 5,827,298 A | 10/1998 | Hart et al. |
| 5,830,125 A | 11/1998 | Scribner et al. |
| 5,830,221 A | 11/1998 | Stein et al. |
| 5,833,698 A | 11/1998 | Hinchliffe et al. |
| 5,843,167 A | 12/1998 | Dwyer et al. |
| 5,845,657 A | 12/1998 | Carberry et al. |
| 5,853,421 A | 12/1998 | Leschinsky et al. |
| 5,853,422 A | 12/1998 | Huebsch et al. |
| 5,855,312 A | 1/1999 | Toledano |
| 5,858,082 A | 1/1999 | Cruz et al. |
| 5,860,991 A | 1/1999 | Klein et al. |
| 5,861,005 A | 1/1999 | Kontos |
| 5,861,043 A | 1/1999 | Carn |
| 5,868,755 A | 2/1999 | Kanner et al. |
| 5,868,762 A | 2/1999 | Cragg et al. |
| 5,868,763 A | 2/1999 | Spence et al. |
| 5,871,474 A | 2/1999 | Hermann et al. |
| 5,871,501 A | 2/1999 | Leschinsky et al. |
| 5,871,525 A | 2/1999 | Edwards et al. |
| 5,873,876 A | 2/1999 | Christy |
| 5,873,891 A | 2/1999 | Sohn |
| 5,879,366 A | 3/1999 | Shaw et al. |
| 5,891,088 A | 4/1999 | Thompson et al. |
| 5,897,487 A | 4/1999 | Ouchi |
| 5,902,310 A | 5/1999 | Foerster et al. |
| 5,904,697 A | 5/1999 | Gifford, III et al. |
| 5,906,631 A | 5/1999 | Imran |
| 5,907,893 A | 6/1999 | Zadno-Azizi et al. |
| 5,910,155 A | 6/1999 | Ratcliff et al. |
| 5,919,207 A | 7/1999 | Taheri |
| 5,922,009 A | 7/1999 | Epstein et al. |
| 5,928,231 A | 7/1999 | Klein et al. |
| 5,928,251 A | 7/1999 | Aranyi et al. |
| 5,935,147 A | 8/1999 | Kensey et al. |
| 5,938,667 A | 8/1999 | Peyser et al. |
| 5,941,890 A | 8/1999 | Voegele et al. |
| 5,947,999 A | 9/1999 | Groiso |
| 5,948,001 A | 9/1999 | Larsen |
| 5,951,518 A | 9/1999 | Licata et al. |
| 5,951,575 A | 9/1999 | Bolduc et al. |
| 5,951,576 A | 9/1999 | Wakabayashi |
| 5,951,589 A | 9/1999 | Epstein et al. |
| 5,957,900 A | 9/1999 | Ouchi |
| 5,957,936 A | 9/1999 | Yoon et al. |
| 5,957,938 A | 9/1999 | Zhu et al. |
| 5,957,940 A | 9/1999 | Tanner et al. |
| 5,964,782 A | 10/1999 | Lafontaine et al. |
| 5,972,034 A | 10/1999 | Hofmann et al. |
| 5,976,161 A | 11/1999 | Kirsch et al. |
| 5,984,934 A | 11/1999 | Ashby et al. |
| 5,984,948 A | 11/1999 | Hasson |
| 5,984,949 A | 11/1999 | Levin |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. |
| 6,010,517 A | 1/2000 | Baccaro |
| 6,013,084 A | 1/2000 | Ken et al. |
| 6,015,815 A | 1/2000 | Mollison |
| 6,019,779 A | 2/2000 | Thorud et al. |
| 6,022,372 A | 2/2000 | Kontos |
| 6,024,750 A | 2/2000 | Mastri et al. |
| 6,024,756 A | 2/2000 | Huebsch et al. |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |
| 6,071,300 A | 6/2000 | Brenneman et al. |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,090,130 A | 7/2000 | Nash et al. |
| 6,095,155 A | 8/2000 | Criscuolo |
| 6,102,271 A | 8/2000 | Longo et al. |
| 6,110,184 A | 8/2000 | Weadock |
| 6,113,610 A | 9/2000 | Poncet |
| 6,113,612 A | 9/2000 | Swanson et al. |
| 6,117,125 A | 9/2000 | Rothbarth et al. |
| 6,117,148 A | 9/2000 | Ravo |
| 6,117,157 A | 9/2000 | Tekulve |
| 6,117,159 A | 9/2000 | Huebsch et al. |
| 6,120,524 A | 9/2000 | Taheri |
| 6,126,675 A | 10/2000 | Schervinsky et al. |
| 6,136,010 A | 10/2000 | Modesitt et al. |
| 6,146,385 A | 11/2000 | Torrie et al. |
| 6,149,660 A | 11/2000 | Laufer et al. |
| 6,149,667 A | 11/2000 | Hovland et al. |
| 6,152,144 A | 11/2000 | Lesh et al. |
| 6,152,936 A | 11/2000 | Christy et al. |
| 6,152,937 A | 11/2000 | Peterson et al. |
| 6,161,263 A | 12/2000 | Anderson |
| 6,165,204 A | 12/2000 | Levinson et al. |
| 6,171,277 B1 | 1/2001 | Ponzi |
| 6,171,329 B1 | 1/2001 | Shaw et al. |
| 6,174,322 B1 | 1/2001 | Schneidt |
| 6,179,849 B1 | 1/2001 | Yencho et al. |
| 6,179,860 B1 | 1/2001 | Fulton, III et al. |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,200,330 B1 | 3/2001 | Benderev et al. |
| 6,206,895 B1 | 3/2001 | Levinson |
| 6,206,913 B1 | 3/2001 | Yencho et al. |
| 6,206,931 B1 | 3/2001 | Cook et al. |
| 6,210,407 B1 | 4/2001 | Webster |

(56) References Cited

U.S. PATENT DOCUMENTS

| | | |
|---|---|---|
| 6,220,248 B1 | 4/2001 | Voegele et al. |
| 6,221,102 B1 | 4/2001 | Baker et al. |
| 6,231,561 B1 | 5/2001 | Frazier et al. |
| 6,245,079 B1 | 6/2001 | Nobles et al. |
| 6,248,124 B1 | 6/2001 | Pedros et al. |
| 6,254,617 B1 | 7/2001 | Spence et al. |
| 6,254,642 B1 | 7/2001 | Taylor |
| 6,258,115 B1 | 7/2001 | Dubrul |
| 6,267,773 B1 | 7/2001 | Gadberry et al. |
| 6,273,903 B1 | 8/2001 | Wilk |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,296,657 B1 | 10/2001 | Brucker |
| 6,302,898 B1 | 10/2001 | Edwards et al. |
| 6,305,891 B1 | 10/2001 | Burlingame |
| 6,309,416 B1 | 10/2001 | Swanson et al. |
| 6,319,258 B1 | 11/2001 | McAllen, III et al. |
| 6,322,580 B1 | 11/2001 | Kanner |
| 6,328,727 B1 | 12/2001 | Frazier et al. |
| 6,329,386 B1 | 12/2001 | Mollison |
| 6,334,865 B1 | 1/2002 | Redmond et al. |
| 6,348,064 B1 | 2/2002 | Kanner |
| 6,355,052 B1 | 3/2002 | Neuss et al. |
| 6,358,258 B1 | 3/2002 | Arcia et al. |
| 6,375,671 B1 | 4/2002 | Kobayashi et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,421,899 B1 | 7/2002 | Zitnay |
| 6,423,054 B1 | 7/2002 | Ouchi |
| 6,425,911 B1 | 7/2002 | Akerfeldt et al. |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,458,130 B1 | 10/2002 | Frazier et al. |
| 6,461,364 B1 | 10/2002 | Ginn et al. |
| 6,482,224 B1 | 11/2002 | Michler et al. |
| 6,488,692 B1 | 12/2002 | Spence et al. |
| 6,500,115 B2 | 12/2002 | Krattiger et al. |
| 6,506,210 B1 | 1/2003 | Kanner |
| 6,508,828 B1 | 1/2003 | Akerfeldt et al. |
| 6,514,280 B1 | 2/2003 | Gilson |
| 6,517,555 B1 | 2/2003 | Caro |
| 6,517,569 B2 | 2/2003 | Mikus et al. |
| 6,527,737 B2 | 3/2003 | Kaneshige |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,547,806 B1 | 4/2003 | Ding |
| 6,551,319 B2 | 4/2003 | Lieberman |
| 6,558,349 B1 | 5/2003 | Kirkman |
| 6,569,173 B1 | 5/2003 | Blatter et al. |
| 6,569,185 B2 | 5/2003 | Ungs |
| 6,572,629 B2 | 6/2003 | Kalloo et al. |
| 6,578,585 B1 | 6/2003 | Stachowski et al. |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,613,060 B2 | 9/2003 | Adams et al. |
| 6,616,686 B2 | 9/2003 | Coleman et al. |
| 6,620,165 B2 | 9/2003 | Wellisz |
| 6,623,509 B2 | 9/2003 | Ginn |
| 6,623,510 B2 | 9/2003 | Carley et al. |
| 6,626,918 B1 | 9/2003 | Ginn et al. |
| 6,626,919 B1 | 9/2003 | Swanstrom |
| 6,626,920 B2 | 9/2003 | Whayne |
| 6,632,197 B2 | 10/2003 | Lyon |
| 6,632,238 B2 | 10/2003 | Ginn et al. |
| 6,634,537 B2 | 10/2003 | Chen |
| 6,645,205 B2 | 11/2003 | Ginn |
| 6,645,225 B1 | 11/2003 | Atkinson |
| 6,652,538 B2 | 11/2003 | Kayan et al. |
| 6,652,556 B1 | 11/2003 | VanTassel et al. |
| 6,663,633 B1 | 12/2003 | Pierson, III |
| 6,663,655 B2 | 12/2003 | Ginn et al. |
| 6,669,714 B2 | 12/2003 | Coleman et al. |
| 6,673,083 B1 | 1/2004 | Kayan et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,685,707 B2 | 2/2004 | Roman et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |
| 6,719,777 B2 | 4/2004 | Ginn et al. |
| 6,726,704 B1 | 4/2004 | Loshakove et al. |
| 6,736,822 B2 | 5/2004 | McClellan et al. |
| 6,743,195 B2 | 6/2004 | Zucker |
| 6,743,243 B1 | 6/2004 | Roy et al. |
| 6,743,259 B2 | 6/2004 | Ginn |
| 6,746,472 B2 | 6/2004 | Frazier et al. |
| 6,749,621 B2 | 6/2004 | Pantages et al. |
| 6,749,622 B2 | 6/2004 | McGuckin et al. |
| 6,752,813 B2 | 6/2004 | Goldfarb et al. |
| 6,755,842 B2 | 6/2004 | Kanner et al. |
| 6,767,356 B2 | 7/2004 | Kanner et al. |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,893 B2 | 1/2005 | Miller |
| 6,837,906 B2 | 1/2005 | Ginn |
| 6,846,319 B2 | 1/2005 | Ginn et al. |
| 6,849,078 B2 | 2/2005 | Durgin et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,904,647 B2 | 6/2005 | Byers, Jr. |
| 6,913,607 B2 | 7/2005 | Ainsworth et al. |
| 6,926,723 B1 | 8/2005 | Mulhauser et al. |
| 6,926,731 B2 | 8/2005 | Coleman et al. |
| 6,929,634 B2 | 8/2005 | Dorros et al. |
| 6,942,641 B2 | 9/2005 | Seddon |
| 6,942,674 B2 | 9/2005 | Belef et al. |
| 6,942,691 B1 | 9/2005 | Chuter |
| 6,964,668 B2 | 11/2005 | Modesitt et al. |
| 6,969,397 B2 | 11/2005 | Ginn |
| 6,984,238 B2 | 1/2006 | Gifford, III et al. |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,025,776 B1 | 4/2006 | Houser et al. |
| 7,033,379 B2 | 4/2006 | Peterson |
| 7,060,084 B1 | 6/2006 | Loshakove et al. |
| 7,063,711 B1 | 6/2006 | Loshakove et al. |
| 7,074,232 B2 | 7/2006 | Kanner et al. |
| 7,076,305 B2 | 7/2006 | Imran et al. |
| 7,083,635 B2 | 8/2006 | Ginn |
| 7,087,064 B1 | 8/2006 | Hyde |
| 7,108,709 B2 | 9/2006 | Cummins |
| 7,111,768 B2 | 9/2006 | Cummins et al. |
| 7,112,225 B2 | 9/2006 | Ginn |
| 7,144,411 B2 | 12/2006 | Ginn et al. |

(56) References Cited

U.S. PATENT DOCUMENTS

| | | |
|---|---|---|
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et |
| 7,229,452 B2 | 6/2007 | Kayan |
| 7,261,716 B2 | 8/2007 | Strobel et al. |
| 7,306,614 B2 | 12/2007 | Weller et al. |
| 7,311,720 B2 | 12/2007 | Mueller et al. |
| 7,316,704 B2 | 1/2008 | Bagaoisan et al. |
| 7,316,706 B2 | 1/2008 | Bloom et al. |
| 7,322,995 B2 | 1/2008 | Buckman et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walburg et al. |
| 7,361,178 B2 | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,431,729 B2 | 10/2008 | Chanduszko |
| 7,465,286 B2 | 12/2008 | Patterson et al. |
| 7,533,790 B1 | 5/2009 | Knodel et al. |
| 7,582,103 B2 | 9/2009 | Young et al. |
| 7,582,104 B2 | 9/2009 | Corcoran et al. |
| 7,597,706 B2 | 10/2009 | Kanner et al. |
| 7,618,427 B2 | 11/2009 | Ortiz et al. |
| 7,622,628 B2 | 11/2009 | Bergin et al. |
| 7,645,285 B2 | 1/2010 | Cosgrove et al. |
| D611,144 S | 3/2010 | Reynolds |
| 7,780,696 B2 | 8/2010 | Daniel et al. |
| 7,799,042 B2 | 9/2010 | Williamson, IV et al. |
| 7,806,904 B2 | 10/2010 | Carley et al. |
| 7,819,895 B2 | 10/2010 | Ginn et al. |
| 7,841,502 B2 | 11/2010 | Walberg et al. |
| 7,842,068 B2 | 11/2010 | Ginn |
| 7,850,709 B2 | 12/2010 | Cummins et al. |
| 7,850,797 B2 | 12/2010 | Carley et al. |
| 7,854,810 B2 | 12/2010 | Carley et al. |
| 7,857,828 B2 | 12/2010 | Jabba et al. |
| 7,867,249 B2 | 1/2011 | Palermo et al. |
| 7,879,071 B2 | 2/2011 | Carley et al. |
| 7,887,555 B2 | 2/2011 | Carley et al. |
| 7,887,563 B2 | 2/2011 | Cummins |
| 7,901,428 B2 | 3/2011 | Ginn et al. |
| 7,905,900 B2 | 3/2011 | Palermo |
| 7,918,873 B2 | 4/2011 | Cummins |
| 7,931,669 B2 | 4/2011 | Ginn et al. |
| 7,931,671 B2 | 4/2011 | Tenerz |
| 7,967,842 B2 | 6/2011 | Bakos |
| 8,007,512 B2 | 8/2011 | Ginn et al. |
| 8,103,327 B2 | 1/2012 | Harlev et al. |
| 8,105,352 B2 | 1/2012 | Egnelov |
| 8,128,644 B2 | 3/2012 | Carley et al. |
| 8,182,497 B2 | 5/2012 | Carley et al. |
| 8,192,459 B2 | 6/2012 | Cummins et al. |
| 8,202,283 B2 | 6/2012 | Carley et al. |
| 8,202,293 B2 | 6/2012 | Ellingwood et al. |
| 8,202,294 B2 | 6/2012 | Jabba et al. |
| 8,226,666 B2 | 7/2012 | Zarbatany et al. |
| 8,226,681 B2 | 7/2012 | Clark et al. |
| 8,236,026 B2 | 8/2012 | Carley et al. |
| 8,257,390 B2 | 9/2012 | Carley et al. |
| 8,303,624 B2 | 11/2012 | Fortson |
| 8,313,497 B2 | 11/2012 | Walberg et al. |
| 8,323,312 B2 | 12/2012 | Clark |
| 8,398,656 B2 | 3/2013 | Palermo et al. |
| 8,398,676 B2 | 3/2013 | Roorda et al. |
| 2001/0007077 A1 | 7/2001 | Ginn et al. |
| 2001/0031972 A1 | 10/2001 | Robertson et al. |
| 2001/0031973 A1 | 10/2001 | Nobles et al. |
| 2001/0044639 A1 | 11/2001 | Levinson |
| 2001/0046518 A1 | 11/2001 | Sawhney |
| 2001/0047180 A1 | 11/2001 | Grudem et al. |
| 2002/0022822 A1 | 2/2002 | Cragg et al. |
| 2002/0026215 A1 | 2/2002 | Redmond et al. |
| 2002/0026216 A1 | 2/2002 | Grimes |
| 2002/0029050 A1 | 3/2002 | Gifford, III et al. |
| 2002/0038127 A1 | 3/2002 | Blatter et al. |
| 2002/0042622 A1 | 4/2002 | Vargas et al. |
| 2002/0049427 A1 | 4/2002 | Wiener et al. |
| 2002/0058960 A1 | 5/2002 | Hudson et al. |
| 2002/0062104 A1 | 5/2002 | Ashby et al. |
| 2002/0077657 A1 | 6/2002 | Ginn et al. |
| 2002/0082641 A1 | 6/2002 | Ginn et al. |
| 2002/0095181 A1 | 7/2002 | Beyar |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0151921 A1 | 10/2002 | Kanner et al. |
| 2002/0151963 A1 | 10/2002 | Brown et al. |
| 2002/0183786 A1 | 12/2002 | Girton |
| 2002/0183787 A1 | 12/2002 | Wahr et al. |
| 2002/0198562 A1 | 12/2002 | Akerfeldt et al. |
| 2002/0198589 A1 | 12/2002 | Leong |
| 2003/0004543 A1 | 1/2003 | Gleeson et al. |
| 2003/0009180 A1 | 1/2003 | Hinchliffe et al. |
| 2003/0023248 A1 | 1/2003 | Parodi |
| 2003/0032981 A1 | 2/2003 | Kanner et al. |
| 2003/0033006 A1 | 2/2003 | Phillips et al. |
| 2003/0045893 A1 | 3/2003 | Ginn |
| 2003/0055455 A1 | 3/2003 | Yang et al. |
| 2003/0060846 A1 | 3/2003 | Egnelov et al. |
| 2003/0065358 A1 | 4/2003 | Frecker et al. |
| 2003/0083679 A1 | 5/2003 | Grudem et al. |
| 2003/0093096 A1 | 5/2003 | McGuckin et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0144695 A1 | 7/2003 | McGuckin, Jr. et al. |
| 2003/0158577 A1 | 8/2003 | Pantages et al. |
| 2003/0158578 A1 | 8/2003 | Pantages et al. |
| 2003/0195504 A1 | 10/2003 | Tallarida et al. |
| 2003/0208211 A1 | 11/2003 | Kortenbach |
| 2004/0009205 A1 | 1/2004 | Sawhney |
| 2004/0044350 A1 | 3/2004 | Martin et al. |
| 2004/0049224 A1 | 3/2004 | Buehlmann et al. |
| 2004/0059376 A1 | 3/2004 | Breuniger |
| 2004/0068273 A1 | 4/2004 | Fariss et al. |
| 2004/0078053 A1 | 4/2004 | Berg et al. |
| 2004/0082906 A1 | 4/2004 | Tallarida et al. |
| 2004/0087985 A1 | 5/2004 | Loshakove et al. |
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0092973 A1 | 5/2004 | Chanduszko et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0106980 A1 | 6/2004 | Solovay et al. |
| 2004/0127940 A1 | 7/2004 | Ginn et al. |
| 2004/0143290 A1 | 7/2004 | Brightbill |
| 2004/0143291 A1 | 7/2004 | Corcoran et al. |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0167570 A1 | 8/2004 | Pantages et al. |
| 2004/0191277 A1 | 9/2004 | Sawhney et al. |
| 2004/0215232 A1 | 10/2004 | Belhe et al. |
| 2004/0243216 A1 | 12/2004 | Gregorich |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravikumar |

(56) References Cited

U.S. PATENT DOCUMENTS

| | | |
|---|---|---|
| 2005/0119695 A1 | 6/2005 | Carley et al. |
| 2005/0121042 A1 | 6/2005 | Belhe et al. |
| 2005/0149117 A1 | 7/2005 | Khosravi et al. |
| 2005/0152949 A1 | 7/2005 | Hotchkiss et al. |
| 2005/0154401 A1 | 7/2005 | Weldon et al. |
| 2005/0165357 A1 | 7/2005 | McGuckin et al. |
| 2005/0169974 A1 | 8/2005 | Tenerez et al. |
| 2005/0177189 A1 | 8/2005 | Ginn et al. |
| 2005/0187564 A1 | 8/2005 | Jayaraman |
| 2005/0203552 A1 | 9/2005 | Laufer et al. |
| 2005/0216057 A1 | 9/2005 | Coleman et al. |
| 2005/0222614 A1 | 10/2005 | Ginn et al. |
| 2005/0228443 A1 | 10/2005 | Yassinzadeh |
| 2005/0245876 A1 | 11/2005 | Khosravi et al. |
| 2005/0267528 A1 | 12/2005 | Ginn et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0064115 A1 | 3/2006 | Allen et al. |
| 2006/0100664 A1 | 5/2006 | Pai et al. |
| 2006/0142784 A1 | 6/2006 | Kontos |
| 2006/0190014 A1 | 8/2006 | Ginn et al. |
| 2006/0190036 A1 | 8/2006 | Wendel et al. |
| 2006/0190037 A1 | 8/2006 | Ginn et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0206146 A1 | 9/2006 | Tenerez |
| 2006/0253037 A1 | 11/2006 | Ginn et al. |
| 2006/0253072 A1 | 11/2006 | Pai et al. |
| 2006/0287674 A1 | 12/2006 | Ginn et al. |
| 2006/0293698 A1 | 12/2006 | Douk |
| 2007/0005093 A1 | 1/2007 | Cox |
| 2007/0010853 A1 | 1/2007 | Ginn et al. |
| 2007/0021778 A1 | 1/2007 | Carly |
| 2007/0027525 A1 | 2/2007 | Ben-Muvhar |
| 2007/0049968 A1 | 3/2007 | Sibbitt, Jr. et al. |
| 2007/0049970 A1 | 3/2007 | Belef et al. |
| 2007/0060895 A1 | 3/2007 | Sibbitt, Jr. et al. |
| 2007/0060950 A1 | 3/2007 | Khosravi et al. |
| 2007/0060951 A1 | 3/2007 | Shannon |
| 2007/0083230 A1 | 4/2007 | Javois |
| 2007/0083231 A1 | 4/2007 | Lee |
| 2007/0112304 A1 | 5/2007 | Voss |
| 2007/0112365 A1 | 5/2007 | Hilal et al. |
| 2007/0112385 A1 | 5/2007 | Conlon |
| 2007/0123816 A1* | 5/2007 | Zhu et al. .................. 604/57 |
| 2007/0123817 A1 | 5/2007 | Khosravi et al. |
| 2007/0123936 A1 | 5/2007 | Goldin et al. |
| 2007/0172430 A1 | 7/2007 | Brito et al. |
| 2007/0179527 A1 | 8/2007 | Eskuri et al. |
| 2007/0185530 A1 | 8/2007 | Chin-Chen et al. |
| 2007/0203507 A1 | 8/2007 | McLaughlin et al. |
| 2007/0213747 A1 | 9/2007 | Monassevitch et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0270904 A1 | 11/2007 | Ginn |
| 2007/0275036 A1 | 11/2007 | Green, III et al. |
| 2007/0276488 A1 | 11/2007 | Wachter et al. |
| 2007/0282352 A1 | 12/2007 | Carley et al. |
| 2007/0282373 A1 | 12/2007 | Ashby et al. |
| 2008/0004640 A1 | 1/2008 | Ellingwood |
| 2008/0009794 A1 | 1/2008 | Bagaoisan et al. |
| 2008/0033459 A1 | 2/2008 | Shafi et al. |
| 2008/0058839 A1 | 3/2008 | Nobles et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0093414 A1 | 4/2008 | Bender et al. |
| 2008/0114378 A1 | 5/2008 | Matsushita |
| 2008/0114395 A1 | 5/2008 | Mathisen et al. |
| 2008/0177288 A1 | 7/2008 | Carlson |
| 2008/0210737 A1 | 9/2008 | Ginn et al. |
| 2008/0221616 A1 | 9/2008 | Ginn et al. |
| 2008/0243148 A1 | 10/2008 | Mikkaichi et al. |
| 2008/0243182 A1 | 10/2008 | Bates et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0287988 A1 | 11/2008 | Smith et al. |
| 2008/0300628 A1 | 12/2008 | Ellingwood |
| 2008/0312686 A1 | 12/2008 | Ellingwood |
| 2008/0312740 A1 | 12/2008 | Wachter et al. |
| 2009/0054912 A1 | 2/2009 | Heanue et al. |
| 2009/0105728 A1 | 4/2009 | Noda et al. |
| 2009/0112306 A1 | 4/2009 | Bonsignore et al. |
| 2009/0137900 A1 | 5/2009 | Bonner et al. |
| 2009/0157101 A1 | 6/2009 | Reyes et al. |
| 2009/0157102 A1 | 6/2009 | Reynolds et al. |
| 2009/0171388 A1 | 7/2009 | Dave et al. |
| 2009/0177212 A1 | 7/2009 | Carley et al. |
| 2009/0187215 A1 | 7/2009 | Mackiewicz et al. |
| 2009/0216267 A1 | 8/2009 | Willard et al. |
| 2009/0227938 A1 | 9/2009 | Fasching et al. |
| 2009/0230168 A1 | 9/2009 | Coleman et al. |
| 2009/0254119 A1 | 10/2009 | Sibbitt, Jr. et al. |
| 2009/0287244 A1 | 11/2009 | Kokish |
| 2009/0312789 A1 | 12/2009 | Kassab et al. |
| 2010/0114156 A1 | 5/2010 | Mehl |
| 2010/0168790 A1 | 7/2010 | Clark |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185234 A1 | 7/2010 | Fortson et al. |
| 2010/0217132 A1 | 8/2010 | Ellingwood et al. |
| 2010/0249828 A1 | 9/2010 | Mavani et al. |
| 2011/0054492 A1 | 3/2011 | Clark |
| 2011/0066163 A1 | 3/2011 | Cho et al. |
| 2011/0066164 A1 | 3/2011 | Walberg et al. |
| 2011/0071565 A1 | 3/2011 | Ginn |
| 2011/0106148 A1 | 5/2011 | Ginn et al. |
| 2011/0137340 A1 | 6/2011 | Cummins |
| 2011/0144691 A1 | 6/2011 | Cummins |
| 2011/0166584 A1 | 7/2011 | Palermo et al. |
| 2011/0178548 A1 | 7/2011 | Tenerz |
| 2011/0218568 A1 | 9/2011 | Voss |
| 2011/0238089 A1 | 9/2011 | Reyes et al. |
| 2011/0270282 A1 | 11/2011 | Lemke |
| 2011/0288563 A1 | 11/2011 | Gianotti et al. |
| 2011/0313452 A1 | 12/2011 | Carley et al. |
| 2012/0029555 A1 | 2/2012 | Fortson et al. |
| 2012/0035630 A1 | 2/2012 | Roorda |
| 2012/0143216 A1 | 6/2012 | Voss |
| 2012/0209317 A1 | 8/2012 | Von Oepen |
| 2012/0245603 A1 | 9/2012 | Voss |
| 2012/0245626 A1 | 9/2012 | Ellingwood et al. |
| 2012/0255655 A1 | 10/2012 | Carley et al. |
| 2012/0296372 A1 | 11/2012 | Ziobro |
| 2012/0310261 A1 | 12/2012 | Cummins et al. |
| 2013/0006274 A1 | 1/2013 | Walberg et al. |

FOREIGN PATENT DOCUMENTS

| | | |
|---|---|---|
| DE | 197 11 288 | 10/1998 |
| DE | 29723736 U1 | 4/1999 |
| DE | 19859952 | 2/2000 |
| DE | 102006056283 | 6/2008 |
| EP | 0 386 361 | 9/1990 |
| EP | 0 534 696 | 3/1993 |
| EP | 0 621 032 | 10/1994 |
| EP | 0 756 851 | 2/1997 |
| EP | 0 774 237 | 5/1997 |

(56) References Cited

FOREIGN PATENT DOCUMENTS

| | | |
|---|---|---|
| EP | 0 858 776 | 8/1998 |
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| GB | 2 397 240 | 7/2004 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 58-181006 | 12/1983 |
| JP | 12 74750 | 11/1989 |
| JP | 11500642 | 8/1997 |
| JP | 2000102546 | 4/2000 |
| NL | 9302140 | 7/1995 |
| PL | 171425 | 4/1997 |
| RU | 2086192 | 8/1997 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/40849 | 8/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/62234 | 8/2002 |
| WO | WO 02/98302 | 12/2002 |
| WO | WO 03/13363 | 2/2003 |
| WO | WO 03/13364 | 2/2003 |
| WO | WO 03/47434 | 6/2003 |
| WO | WO 03/71955 | 9/2003 |
| WO | WO 03/71956 | 9/2003 |
| WO | WO 03/71957 | 9/2003 |
| WO | WO 03/94748 | 11/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/05585 | 1/2007 |
| WO | WO 2007/25014 | 3/2007 |
| WO | WO 2007/81836 | 7/2007 |
| WO | WO 2007/88069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

U.S. Appl. No. 11/396,141, Mail Date Apr. 30, 2013, Office Action.
U.S. Appl. No. 11/852,190, Mail Date Apr. 24, 2013, Office Action.
U.S. Appl. No. 12/848,642, Mail Date Apr. 26, 2013, Office Action.
U.S. Appl. No. 12/850,242, Mail Date Apr. 18, 2013, Office Action.
U.S. Appl. No. 12/955,859, Mail Date May 16, 2013, Office Action.
U.S. Appl. No. 13/052,634, Mail Date Feb. 8, 2013, Office Action.
U.S. Appl. No. 13/052,634, Mail Date Apr. 22, 2013, Office Action.
U.S. Appl. No. 13/488,233, Mail Date May 15, 2013, Issue Notification.
U.S. Appl. No. 13/490,143, Mail Date Apr. 29, 2013, Notice of Allowance.
U.S. Appl. No. 09/610,128, filed Jul. 5, 2000, Kerievsky.
U.S. Appl. No. 09/866,551, filed May 25, 2001, Ginn.
U.S. Appl. No. 12/113,092, filed Apr. 30, 2008, Ginn et al.
U.S. Appl. No. 13/017,636, filed Jan. 31, 2011, Carley et al.
U.S. Appl. No. 13/308,227, filed Nov. 30, 2011, Yibarren.
U.S. Appl. No. 13/791,846, filed Mar. 8, 2013, Palermo.
U.S. Appl. No. 60/693,531, filed Jun. 24, 2005, Carly.
U.S. Appl. No. 60/696,069, filed Jul. 1, 2005, Pantages et al.
U.S. Appl. No. 60/793,444, filed Apr. 20, 2006, Jones et al.
U.S. Appl. No. 60/946,026, filed Jun. 25, 2007, Ellingwood.
U.S. Appl. No. 60/946,030, filed Jun. 25, 2007, Voss et al.

(56) References Cited

OTHER PUBLICATIONS

U.S. Appl. No. 60/946,042, filed Jun. 25, 2007, Ellingwood et al.
U.S. Appl. No. 61/015,144, filed Dec. 19, 2007, Mackiewicz et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
"Hand tool for forming telephone connections—comprises pliers with reciprocably driven ram crimping clip around conductors against anvil", Derwent-ACC-No. 1978-B8090A.
Database WPI; Section PQ, Week 200120; Derwent Publications Ltd., London GB; Class P31, AN 2001-203165; XP002199926 & ZA 200 100 528 A (Anthony T), Feb. 28, 2001 abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DI Wessel et al, Outpatient closure of the patent ductus arteriosus, Circulation, May 1988, pp. 1068-1071, vol. 77—No. 5, Department of Anasthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D., Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PHD, Wound Closure Biomaterials and Devices, Shock., Mar. 1999, p. 226, vol. 11—No. 3, Institution Northwestern University (editorial review).
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul 1996, pp. 449-451, vol. 27—No. 6, Department of Surgery, Mercy Hospital of Pittsburgh, PA.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.
Inlet Medical Inc. Brochure, pp. 1-2, referencing Om Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.
ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radio!., Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.
Stretch Comb by Scunci, retrieved via internet at www.scunci.com/productdetail by examiner on Oct. 9, 2007, publication date unavailable.
Swee Lian Tan, MD, PHD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.
Sy Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Taber's Cyclopedic Medical Dictionary, 18th Ed. 1997, pp. 747 and 1420.
Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.
Tomoaki Hinohara, Percutaneous vascular surgery (Prostar® Plus and Techstar® for femoral artery site closure), Interventional Cardiology Newsletter, May-Jul. 1997, pp. 19-22, pp. 24-28, vol. 5—No. 3-4.
Ut Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.
Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.
William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.

(56) References Cited

OTHER PUBLICATIONS

U.S. Appl. No. 09/478,179, Mail Date Nov. 6, 2000, Notice of Allowance.
U.S. Appl. No. 09/546,998, Mail Date May 6, 2002, Notice of Allowance.
U.S. Appl. No. 09/610,238, Mail Date Mar. 26, 2001, Notice of Allowance.
U.S. Appl. No. 09/610,238, Mail Date Sep. 5, 2001, Office Action.
U.S. Appl. No. 09/610,238, Mail Date Feb. 11, 2002, Notice of Allowance.
U.S. Appl. No. 09/680,837, Mail Date Jul. 9, 2002, Office Action.
U.S. Appl. No. 09/680,837, Mail Date Nov. 6, 2002, Office Action.
U.S. Appl. No. 09/680,837, Mail Date Mar. 25, 2003, Office Action.
U.S. Appl. No. 09/680,837, Mail Date Jun. 16, 2003, Notice of Allowance.
U.S. Appl. No. 09/732,178, Mail Date Aug. 1, 2002, Office Action.
U.S. Appl. No. 09/732,178, Mail Date Dec. 24, 2002, Office Action.
U.S. Appl. No. 09/732,178, Mail Date Jun. 10, 2003, Office Action.
U.S. Appl. No. 09/732,178, Mail Date Jul. 3, 2003, Office Action.
U.S. Appl. No. 09/732,178, Mail Date Nov. 17, 2003, Notice of Allowance.
U.S. Appl. No. 09/732,835, Mail Date Sep. 11, 2003, Office Action.
U.S. Appl. No. 09/732,835, Mail Date Feb. 9, 2004, Office Action.
U.S. Appl. No. 09/732,835, Mail Date Mar. 17, 2004, Notice of Allowance.
U.S. Appl. No. 09/764,813, Mail Date Mar. 26, 2001, Office Action.
U.S. Appl. No. 09/764,813, Mail Date Jun. 4, 2001, Notice of Allowance.
U.S. Appl. No. 09/933,299, Mail date Feb. 26, 2003, Office Action.
U.S. Appl. No. 09/933,299, Mail Date Jun. 16, 2003, Notice of Allowance.
U.S. Appl. No. 09/948,813, Mail Date Jan. 31, 2003, Notice of Allowance.
U.S. Appl. No. 09/949,398, Mail Date Mar. 4, 2003, Office Action.
U.S. Appl. No. 09/949,398, Mail Date Jul. 28, 2003, Notice of Allowance.
U.S. Appl. No. 09/949,438, Mail Date Dec. 17, 2002, Office Action.
U.S. Appl. No. 09/949,438, Mail Date Apr. 21, 2003, Notice of Allowance.
U.S. Appl. No. 10/006,400, Mail Date Aug. 27, 2004, Office Action.
U.S. Appl. No. 10/006,400, Mail Date Feb. 23, 2005, Office Action.
U.S. Appl. No. 10/006,400, Mail Date Apr. 11, 2005, Office Action.
U.S. Appl. No. 10/006,400, Mail Date Jul. 27, 2005, Office Action.
U.S. Appl. No. 10/006,400, Mail Date Mar. 6, 2006, Office Action.
U.S. Appl. No. 10/006,400, Mail Date May 24, 2006, Office Action.
U.S. Appl. No. 10/006,400, Mail Date Oct. 26, 2006, Office Action.
U.S. Appl. No. 10/006,400, Mail Date Apr. 19, 2007, Office Action.
U.S. Appl. No. 10/006,400, Mail Date Apr. 2, 2008, Office Action.
U.S. Appl. No. 10/006,400, Mail Date Jan. 2, 2009, Office Action.
U.S. Appl. No. 10/006,400, Mail Date Jul. 9, 2009, Notice of Allowance.
U.S. Appl. No. 10/006,400, Mail Date Jan. 13, 2010, Notice of Allowance.
U.S. Appl. No. 10/006,400, Mail Date Apr. 27, 2010, Notice of Allowance.
U.S. Appl. No. 10/006,400, Mail Date Aug. 2, 2010, Notice of Allowance.
U.S. Appl. No. 10/081,717, Mail Date Sep. 29, 2003, Notice of Allowance.
U.S. Appl. No. 10/081,723, Mail Date Sep. 29, 2004, Office Action.
U.S. Appl. No. 10/081,723, Mail Date May 13, 2005, Notice of Allowance.
U.S. Appl. No. 10/081,725, Mail Date Feb. 9, 2004, Notice of Allowance.
U.S. Appl. No. 10/081,725, Mail Date Apr. 13, 2004, Office Action.
U.S. Appl. No. 10/081,726, Mail Date Apr. 11, 2003, Notice of Allowance.
U.S. Appl. No. 10/081,726, Mail Date Jun. 9, 2003, Notice of Allowance.
U.S. Appl. No. 10/147,774, Mail Date Nov. 4, 2004, Office Action.
U.S. Appl. No. 10/147,774, Mail Date May 4, 2005, Office Action.
U.S. Appl. No. 10/147,774, Mail Date Oct. 18, 2005, Office Action.
U.S. Appl. No. 10/147,774, Mail Date Apr. 18, 2007, Notice of Allowance.
U.S. Appl. No. 10/147,774, Mail Date Sep. 27, 2007, Notice of Allowance.
U.S. Appl. No. 10/147,774, Mail Date Feb. 4, 2008, Notice of Allowance.
U.S. Appl. No. 10/147,774, Mail Date Jun. 30, 2008, Office Action.
U.S. Appl. No. 10/147,774, Mail Date Mar. 18, 2009, Office Action.
U.S. Appl. No. 10/147,774, Mail Date Oct. 26, 2009, Office Action.
U.S. Appl. No. 10/147,774, Mail Date Jun. 8, 2010, Office Action.
U.S. Appl. No. 10/147,774, Mail Date Dec. 2, 2010, Notice of Allowance.
U.S. Appl. No. 10/240,183, Mail Date Jul. 27, 2004, Office Action.
U.S. Appl. No. 10/240,183, Mail Date Dec. 17, 2004, Office Action.
U.S. Appl. No. 10/240,183, Mail Date Mar. 9, 2005, Notice of Allowance.
U.S. Appl. No. 10/240,183, Mail Date Aug. 11, 2006, Office Action.
U.S. Appl. No. 10/264,306, Mail Date Feb. 9, 2005, Office Action.
U.S. Appl. No. 10/264,306, Mail Date Oct. 4, 2005, Office Action.
U.S. Appl. No. 10/264,306, Mail Date May 10, 2006, Notice of Allowance.
U.S. Appl. No. 10/264,306, Mail Date Jul. 2, 2007, Notice of Allowance.
U.S. Appl. No. 10/264,306, Mail Date Feb. 4, 2008, Notice of Allowance.
U.S. Appl. No. 10/264,306, Mail Date Jun. 27, 2008, Office Action.
U.S. Appl. No. 10/264,306, Mail Date Feb. 26, 2009, Office Action.
U.S. Appl. No. 10/264,306, Mail Date Aug. 13, 2009, Office Action.
U.S. Appl. No. 10/264,306, Mail Date Jan. 27, 2010, Office Action.
U.S. Appl. No. 10/264,306, Mail Date Jun. 15, 2010, Office Action.
U.S. Appl. No. 10/264,306, Mail Date Oct. 29, 2010, Notice of Allowance.
U.S. Appl. No. 10/335,075, Mail Date Aug. 10, 2005, Office Action.
U.S. Appl. No. 10/335,075, Mail Date Dec. 19, 2005, Office Action.
U.S. Appl. No. 10/335,075, Mail Date Apr. 21, 2006, Office Action.
U.S. Appl. No. 10/335,075, Mail Date Dec. 27, 2006, Notice of Allowance.
U.S. Appl. No. 10/356,214, Mail Date Nov. 30, 2005, Office Action.
U.S. Appl. No. 10/356,214, Mail Date Aug. 23, 2006, Office Action.
U.S. Appl. No. 10/356,214, Mail Date Feb. 13, 2007, Office Action.
U.S. Appl. No. 10/356,214, Mail Date Sep. 12, 2007, Office Action.
U.S. Appl. No. 10/356,214, Mail Date Mar. 6, 2008, Office Action.
U.S. Appl. No. 10/356,214, Mail Date Nov. 4, 2008, Office Action.
U.S. Appl. No. 10/356,214, Mail Date Apr. 29, 2009, Office Action.
U.S. Appl. No. 10/356,214, Mail Date Jan. 13, 2010, Notice of Allowance.
U.S. Appl. No. 10/356,214, Mail Date May 13, 2010, Notice of Allowance.
U.S. Appl. No. 10/356,214, Mail Date Sep. 3, 2010, Notice of Allowance.
U.S. Appl. No. 10/435,104, Mail Date Jun. 10, 2004, Office Action.
U.S. Appl. No. 10/435,104, Mail Date Sep. 21, 2004 Notice of Allowance.
U.S. Appl. No. 10/435,104, Mail Date Jan. 3, 2006, Examiner's Amendment.
U.S. Appl. No. 10/435,104, Mail Date May 16, 2006, Office Action.
U.S. Appl. No. 10/435,104, Mail Date Dec. 28, 2006, Notice of Allowance.
U.S. Appl. No. 10/435,104, Mail Date Jul. 10, 2007, Notice of Allowance.
U.S. Appl. No. 10/435,104, Mail Date Aug. 2, 2007, Notice of Allowance.
U.S. Appl. No. 10/435,104, Mail Date Oct. 26, 2007, Notice of Allowance.
U.S. Appl. No. 10/435,104, Mail Date Nov. 14, 2007, Notice of Allowance.
U.S. Appl. No. 10/435,104, Mail Date Apr. 4, 2008, Notice of Allowance.
U.S. Appl. No. 10/435,104, Mail Date Sep. 26, 2008, Notice of Allowance.

(56) References Cited

OTHER PUBLICATIONS

U.S. Appl. No. 10/435,104, Mail Date Dec. 22, 2008, Notice of Allowance.
U.S. Appl. No. 10/435,104, Mail Date Jul. 23, 2009, Notice of Allowance.
U.S. Appl. No. 10/435,104, Mail Date Jan. 20, 2010, Notice of Allowance.
U.S. Appl. No. 10/435,104, Mail Date Jun. 2, 2010, Office Action.
U.S. Appl. No. 10/435,104, Mail Date Oct. 5, 2010, Notice of Allowance.
U.S. Appl. No. 10/455,768, Mail Date Nov. 16, 2004, Office Action.
U.S. Appl. No. 10/455,768, Mail Date Apr. 6, 2005, Notice of Allowance.
U.S. Appl. No. 10/486,067, Mail Date Jan. 10, 2006, Office Action.
U.S. Appl. No. 10/486,067, Mail Date Sep. 20, 2006, Notice of Allowance.
U.S. Appl. No. 10/486,070, Mail Date Apr. 20, 2005, Office Action.
U.S. Appl. No. 10/486,070, Mail Date Aug. 10, 2005, Office Action.
U.S. Appl. No. 10/486,070, Mail Date Oct. 18, 2005, Notice of Allowance.
U.S. Appl. No. 10/517,004, Mail Date Aug. 13, 2007, Office Action.
U.S. Appl. No. 10/517,004, Mail Date Jan. 30, 2008, Office Action.
U.S. Appl. No. 10/517,004, Mail Date Aug. 13, 2008, Notice of Allowance.
U.S. Appl. No. 10/517,004, Mail Date Feb. 10, 2009, Notice of Allowance.
U.S. Appl. No. 10/517,004, Mail Date Mar. 24, 2009, Notice of Allowance.
U.S. Appl. No. 10/517,004, Mail Date Jun. 26, 2009, Notice of Allowance.
U.S. Appl. No. 10/517,004, Mail Date Jan. 11, 2010, Notice of Allowance.
U.S. Appl. No. 10/517,004, Mail Date Apr. 23, 2010, Notice of Allowance.
U.S. Appl. No. 10/517,004, Mail Date Aug. 3, 2010, Notice of Allowance.
U.S. Appl. No. 10/517,004, Mail Date Nov. 23, 2010, Issue Notification.
U.S. Appl. No. 10/519,778, Mail Date Feb. 23, 2006, Office Action.
U.S. Appl. No. 10/519,778, Mail Date May 31, 2006, Notice of Allowance.
U.S. Appl. No. 10/541,083, Mail Date Oct. 16, 2007, Office Action.
U.S. Appl. No. 10/541,083, Mail Date Oct. 31, 2007, Office Action.
U.S. Appl. No. 10/541,083, Mail Date May 5, 2008, Office Action.
U.S. Appl. No. 10/541,083, Mail Date Sep. 19, 2008, Notice of Allowance.
U.S. Appl. No. 10/541,083, Mail Date Dec. 29, 2008, Notice of Allowance.
U.S. Appl. No. 10/541,083, Mail Date Apr. 16, 2009, Notice of Allowance.
U.S. Appl. No. 10/541,083, Mail Date Sep. 30, 2009, Notice of Allowance.
U.S. Appl. No. 10/541,083, Mail Date Feb. 5, 2010, Notice of Allowance.
U.S. Appl. No. 10/541,083, Mail Date May 10, 2010, Notice of Allowance.
U.S. Appl. No. 10/541,083, Mail Date Aug. 17, 2010, Notice of Allowance.
U.S. Appl. No. 10/541,083, Mail Date Dec. 1, 2010, Issue Notification.
U.S. Appl. No. 10/616,832, Mail Date Jun. 30, 2006, Office Action.
U.S. Appl. No. 10/616,832, Mail Date Oct. 20, 2006, Office Action.
U.S. Appl. No. 10/616,832, Mail Date May 29, 2007, Office Action.
U.S. Appl. No. 10/616,832, Mail Date Jan. 22, 2008, Office Action.
U.S. Appl. No. 10/616,832, Mail Date Sep. 17, 2008, Office Action.
U.S. Appl. No. 10/616,832, Mail Date Jul. 21, 2009, Office Action.
U.S. Appl. No. 10/616,832, Mail Date Jan. 11, 2010, Notice of Allowance.
U.S. Appl. No. 10/616,832, Mail Date May 12, 2010, Notice of Allowance.
U.S. Appl. No. 10/616,832, Mail Date Sep. 20, 2010, Notice of Allowance.
U.S. Appl. No. 10/617,090, Mail Date Mar. 22, 2005, Office Action.
U.S. Appl. No. 10/617,090, Mail Date Jul. 6, 2005, Notice of Allowance.
U.S. Appl. No. 10/617,090, Mail Date Oct. 5, 2005, Notice of Allowance.
U.S. Appl. No. 10/638,115, Mail Date Sep. 22, 2006, Office Action.
U.S. Appl. No. 10/638,115, Mail Date Jan. 31, 2007, Office Action.
U.S. Appl. No. 10/638,115, Mail Date Sep. 18, 2007, Office Action.
U.S. Appl. No. 10/638,115, Mail Date Feb. 7, 2008, Office Action.
U.S. Appl. No. 10/638,115, Mail Date Oct. 29, 2008, Office Action.
U.S. Appl. No. 10/638,115, Mail Date May 7, 2009, Notice of Allowance.
U.S. Appl. No. 10/638,115, Mail Date Dec. 1, 2009, Notice of Allowance.
U.S. Appl. No. 10/638,115, Mail Date Apr. 2, 2010, Notice of Allowance.
U.S. Appl. No. 10/638,115, Mail Date Aug. 13, 2010, Notice of Allowance.
U.S. Appl. No. 10/638,115, Mail Date Dec. 22, 2010, Issue Notification.
U.S. Appl. No. 10/667,144, Mail Date Sep. 19, 2006, Office Action.
U.S. Appl. No. 10/667,144, Mail Date May 2, 2007, Office Action.
U.S. Appl. No. 10/667,144, Mail Date Nov. 19, 2007, Office Action.
U.S. Appl. No. 10/667,144, Mail Date Dec. 5, 2007, Office Action.
U.S. Appl. No. 10/667,144, Mail Date May 12, 2008, Office Action.
U.S. Appl. No. 10/667,144, Mail Date Mar. 24, 2009, Office Action.
U.S. Appl. No. 10/667,144, Mail Date Nov. 23, 2009, Office Action.
U.S. Appl. No. 10/667,144, Mail Date Jun. 22, 2010, Office Action.
U.S. Appl. No. 10/667,144, Mail Date Jun. 6, 2011, Office Action.
U.S. Appl. No. 10/667,144, Mail Date Oct. 28, 2011, Notice of Allowance.
U.S. Appl. No. 10/669,313, Mail Date Oct. 31, 2005, Office Action.
U.S. Appl. No. 10/669,313, Mail Date Jan. 11, 2006, Notice of Allowance.
U.S. Appl. No. 10/669,313, Mail Date Jun. 28, 2006, Notice of Allowance.
U.S. Appl. No. 10/682,459, Mail Date Sep. 15, 2006, Office Action.
U.S. Appl. No. 10/682,459, Mail Date Apr. 18, 2007, Office Action.
U.S. Appl. No. 10/682,459, Mail Date Apr. 2, 2008, Office Action.
U.S. Appl. No. 10/682,459, Mail Date Dec. 4, 2008, Office Action.
U.S. Appl. No. 10/682,459, Mail Date Jun. 10, 2009, Office Action.
U.S. Appl. No. 10/682,459, Mail Date Dec. 23, 2009, Office Action.
U.S. Appl. No. 10/682,459, Mail Date Apr. 28, 2010, Office Action.
U.S. Appl. No. 10/682,459, Mail Date Oct. 12, 2010, Office Action.
U.S. Appl. No. 10/682,459, Mail Date Apr. 1, 2011, Notice of Allowance.
U.S. Appl. No. 10/786,444, Mail Date Oct. 30, 2006, Office Action.
U.S. Appl. No. 10/786,444, Mail Date Apr. 17, 2007, Office Action.
U.S. Appl. No. 10/786,444, Mail Date Aug. 31, 2007, Office Action.
U.S. Appl. No. 10/786,444, Mail Date Apr. 24, 2008, Office Action.
U.S. Appl. No. 10/786,444, Mail Date Oct. 17, 2008, Office Action.
U.S. Appl. No. 10/786,444, Mail Date Jun. 18, 2009, Office Action.
U.S. Appl. No. 10/786,444, Mail Date Jan. 14, 2010, Office Action.
U.S. Appl. No. 10/787,073, Mail Date Nov. 30, 2006, Office Action.
U.S. Appl. No. 10/787,073, Mail Date Sep. 5, 2007, Office Action.
U.S. Appl. No. 10/787,073, Mail Date Feb. 22, 2008, Office Action.
U.S. Appl. No. 10/787,073, Mail Date Nov. 12, 2008, Office Action.
U.S. Appl. No. 10/787,073, Mail Date Aug. 13, 2009, Office Action.
U.S. Appl. No. 10/787,073, Mail Date Feb. 17, 2010, Notice of Allowance.
U.S. Appl. No. 10/787,073, Mail Date Aug. 25, 2010, Notice of Allowance.
U.S. Appl. No. 10/787,073, Mail Date Sep. 15, 2010, Issue Notification.
U.S. Appl. No. 10/908,721, Mail Date Oct. 19, 2006, Office Action.
U.S. Appl. No. 10/908,721, Mail Date Aug. 10, 2007, Office Action.
U.S. Appl. No. 10/908,721, Mail Date Jan. 25, 2008, Office Action.
U.S. Appl. No. 10/908,721, Mail Date Nov. 25, 2008, Office Action.
U.S. Appl. No. 10/908,721, Mail Date Jun. 23, 2009, Office Action.
U.S. Appl. No. 10/908,721, Mail Date Feb. 2, 2010, Office Action.
U.S. Appl. No. 11/048,503, Mail Date Mar. 13, 2009, Office Action.

(56) References Cited

OTHER PUBLICATIONS

U.S. Appl. No. 11/048,503, Mail Date Jun. 26, 2009, Office Action.
U.S. Appl. No. 11/048,503, Mail Date Jan. 11, 2010, Notice of Allowance.
U.S. Appl. No. 11/048,503, Mail Date Apr. 26, 2010, Notice of Allowance.
U.S. Appl. No. 11/048,503, Mail Date Jul. 30, 2010, Notice of Allowance.
U.S. Appl. No. 11/048,503, Mail Date Dec. 8, 2010, Issue Notification.
U.S. Appl. No. 11/113,549, Mail Date Feb. 6, 2007, Office Action.
U.S. Appl. No. 11/113,549, Mail Date May 30, 2007, Office Action.
U.S. Appl. No. 11/113,549, Mail Date Nov. 9, 2007, Office Action.
U.S. Appl. No. 11/113,549, Mail Date Apr. 16, 2008, Office Action.
U.S. Appl. No. 11/113,549, Mail Date Jul. 21, 2009, Office Action.
U.S. Appl. No. 11/113,549, Mail Date Jul. 6, 2010, Office Action.
U.S. Appl. No. 11/113,549, Mail Date Jan. 4, 2011, Office Action.
U.S. Appl. No. 11/152,562, Mail Date May 13, 2008, Office Action.
U.S. Appl. No. 11/152,562, Mail Date Feb. 13, 2009, Office Action.
U.S. Appl. No. 11/152,562, Mail Date Jul. 6, 2009, Office Action.
U.S. Appl. No. 11/152,562, Mail Date Mar. 31, 2010, Office Action.
U.S. Appl. No. 11/152,562, Mail Date Sep. 16, 2010, Notice of Allowance.
U.S. Appl. No. 11/198,811, Mail Date Aug. 26, 2008, Office Action.
U.S. Appl. No. 11/198,811, Mail Date Apr. 6, 2009, Office Action.
U.S. Appl. No. 11/198,811, Mail Date Sep. 22, 2009, Office Action.
U.S. Appl. No. 11/198,811, Mail Date Jun. 29, 2010, Notice of Allowance.
U.S. Appl. No. 11/198,811, Mail Date Oct. 20, 2010, Issue Notification.
U.S. Appl. No. 11/344,793, Mail Date Jan. 22, 2009, Office Action.
U.S. Appl. No. 11/344,868, Mail Date Mar. 25, 2009, Office Action.
U.S. Appl. No. 11/344,891, Mail Date Apr. 29, 2008, Office Action.
U.S. Appl. No. 11/344,891, Mail Date Dec. 8, 2008, Office Action.
U.S. Appl. No. 11/344,891, Mail Date Feb. 26, 2009, Office Action.
U.S. Appl. No. 11/344,891, Mail Date Oct. 7, 2009, Office Action.
U.S. Appl. No. 11/344,891, Mail Date May 7, 2010, Office Action.
U.S. Appl. No. 11/344,891, Mail Date Jan. 22, 2013, Notice of Allowance.
U.S. Appl. No. 11/390,586, Mail Date Jun. 24, 2009, Office Action.
U.S. Appl. No. 11/390,586, Mail Date Jul. 6, 2010, Office Action.
U.S. Appl. No. 11/390,586, Mail Date May 3, 2012, Notice of Allowance.
U.S. Appl. No. 11/396,141, Mail Date May 22, 2009, Office Action.
U.S. Appl. No. 11/396,141, Mail Date Aug. 26, 2009, Office Action.
U.S. Appl. No. 11/396,141, Mail Date May 4, 2010, Office Action.
U.S. Appl. No. 11/396,731, Mail Date Feb. 13, 2009, Office Action.
U.S. Appl. No. 11/396,731, Mail Date May 22, 2009, Office Action.
U.S. Appl. No. 11/396,731, Mail Date Jun. 29, 2010, Office Action.
U.S. Appl. No. 11/396,731, Mail Date Mar. 22, 2011, Office Action.
U.S. Appl. No. 11/396,731, Mail Date Sep. 1, 2011, Office Action.
U.S. Appl. No. 11/406,203, Mail Date May 14, 2007, Office Action.
U.S. Appl. No. 11/406,203, Mail Date Jan. 29, 2008, Notice of Allowance.
U.S. Appl. No. 11/406,203, Mail Date May 23, 2008, Notice of Allowance.
U.S. Appl. No. 11/406,203, Mail Date Sep. 22, 2008, Notice of Allowance.
U.S. Appl. No. 11/406,203, Mail Date Mar. 3, 2009, Office Action.
U.S. Appl. No. 11/406,203, Mail Date Sep. 16, 2009, Office Action.
U.S. Appl. No. 11/406,203, Mail Date Jun. 18, 2010, Notice of Allowance.
U.S. Appl. No. 11/406,203, Mail Date Oct. 6, 2010, Issue Notification.
U.S. Appl. No. 11/411,925, Mail Date Jun. 6, 2007, Office Action.
U.S. Appl. No. 11/411,925, Mail Date Feb. 5, 2008, Office Action.
U.S. Appl. No. 11/411,925, Mail Date Jan. 12, 2009, Office Action.
U.S. Appl. No. 11/411,925, Mail Date Sep. 10, 2009, Office Action.
U.S. Appl. No. 11/427,297, Mail Date Jan. 30, 2009, Office Action.
U.S. Appl. No. 11/427,297, Mail Date Sep. 15, 2009, Office Action.
U.S. Appl. No. 11/427,297, Mail Date Sep. 15, 2010, Office Action.
U.S. Appl. No. 11/427,297, Mail Date Mar. 21, 2011, Office Action.
U.S. Appl. No. 11/427,297, Mail Date Jun. 26, 2012, Notice of Allowance.
U.S. Appl. No. 11/427,309, Mail Date May 28, 2008, Office Action.
U.S. Appl. No. 11/427,309, Mail Date Jan. 2, 2009, Office Action.
U.S. Appl. No. 11/427,309, Mail Date Apr. 20, 2009, Office Action.
U.S. Appl. No. 11/427,309, Mail Date Nov. 6, 2009, Office Action.
U.S. Appl. No. 11/427,309, Mail Date Apr. 26, 2010, Office Action.
U.S. Appl. No. 11/427,309, Mail Date Nov. 15, 2010, Office Action.
U.S. Appl. No. 11/455,993, Mail Date Feb. 17, 2009, Office Action.
U.S. Appl. No. 11/455,993, Mail Date Dec. 16, 2009, Office Action.
U.S. Appl. No. 11/532,325, Mail Date Feb. 23, 2009, Office Action.
U.S. Appl. No. 11/532,325, Mail Date Jun. 17, 2009, Office Action.
U.S. Appl. No. 11/532,325, Mail Date Jan. 5, 2010, Office Action.
U.S. Appl. No. 11/532,576, Mail Date Mar. 1, 2010, Office Action.
U.S. Appl. No. 11/532,576, Mail Date Apr. 23, 2010, Office Action.
U.S. Appl. No. 11/532,576, Mail Date Oct. 13, 2010, Notice of Allowance.
U.S. Appl. No. 11/674,930, Mail Date Jan. 8, 2009, Office Action.
U.S. Appl. No. 11/674,930, Mail Date Jun. 4, 2009, Office Action.
U.S. Appl. No. 11/674,930, Mail Date Jan. 8, 2010, Office Action.
U.S. Appl. No. 11/675,462, Mail Date Dec. 10, 2009, Office Action.
U.S. Appl. No. 11/675,462, Mail Date Aug. 31, 2010, Office Action.
U.S. Appl. No. 11/675,462, Mail Date Aug. 3, 2011, Office Action.
U.S. Appl. No. 11/675,462, Mail Date Dec. 22, 2011, Notice of Allowance.
U.S. Appl. No. 11/744,089, Mail Date Nov. 26, 2008, Office Action.
U.S. Appl. No. 11/744,089, Mail Date Aug. 14, 2009 Office Action.
U.S. Appl. No. 11/744,089, Mail Date Aug. 8, 2012 Office Action.
U.S. Appl. No. 11/757,108, Mail Date Nov. 25, 2009, Office Action.
U.S. Appl. No. 11/767,818, Mail Date Dec. 24, 2009, Office Action.
U.S. Appl. No. 11/767,818, Mail Date Mar. 22, 2010, Office Action.
U.S. Appl. No. 11/767,818, Mail Date Sep. 30, 2010, Office Action.
U.S. Appl. No. 11/767,818, Mail Date Feb. 16, 2011, Office Action.
U.S. Appl. No. 11/767,818, Mail Date Feb. 3, 2012, Notice of Allowance.
U.S. Appl. No. 11/852,190, Mail Date Jun. 24, 2010, Office Action.
U.S. Appl. No. 11/852,190, Mail Date Nov. 1, 2010, Office Action.
U.S. Appl. No. 11/852,190, Mail Date Mar. 2, 2011, Office Action.
U.S. Appl. No. 11/958,281, Mail Date Sep. 2, 2010, Office Action.
U.S. Appl. No. 11/958,281, Mail Date Oct. 8, 2010, Office Action.
U.S. Appl. No. 11/958,281, Mail Date Mar. 10, 2011, Office Action.
U.S. Appl. No. 11/958,295, Mail Date Aug. 27, 2009, Office Action.
U.S. Appl. No. 11/958,295, Mail Date May 25, 2010, Office Action.
U.S. Appl. No. 11/959,334, Mail Date Aug. 19, 2009, Office Action.
U.S. Appl. No. 11/959,334, Mail Date Jan. 12, 2010, Notice of Allowance.
U.S. Appl. No. 11/959,334, Mail Date Apr. 14, 2010, Notice of Allowance.
U.S. Appl. No. 11/959,334, Mail Date Jul. 23, 2010, Notice of Allowance.
U.S. Appl. No. 11/959,334, Mail Date Nov. 10, 2010, Issue Notification.
U.S. Appl. No. 12/106,928, Mail Date Jan. 23, 2009, Office Action.
U.S. Appl. No. 12/106,928, Mail Date Oct. 5, 2009, Office Action.
U.S. Appl. No. 12/106,928, Mail Date May 10, 2010, Office Action.
U.S. Appl. No. 12/106,928, Mail Date Oct. 25, 2010, Office Action.
U.S. Appl. No. 12/106,937, Mail Date Mar. 30, 2009, Office Action.
U.S. Appl. No. 12/106,937, Mail Date Nov. 18, 2009, Office Action.
U.S. Appl. No. 12/113,851, Mail Date Apr. 27, 2010, Office Action.
U.S. Appl. No. 12/113,851, Mail Date Jun. 24, 2010, Office Action.
U.S. Appl. No. 12/113,851, Mail Date Dec. 16, 2010, Office Action.
U.S. Appl. No. 12/113,851, Mail Date Apr. 27, 2011, Office Action.
U.S. Appl. No. 12/113,851, Mail Date Mar. 29, 2012, Office Action.
U.S. Appl. No. 12/114,031, Mail Date Oct. 5, 2010, Office Action.
U.S. Appl. No. 12/114,031, Mail Date Nov. 22, 2010, Office Action.
U.S. Appl. No. 12/114,031, Mail Date May 11, 2011, Office Action.
U.S. Appl. No. 12/114,031, Mail Date Aug. 2, 2011, Office Action.
U.S. Appl. No. 12/114,031, Mail Date Mar. 6, 2012, Office Action.
U.S. Appl. No. 12/114,091, Mail Date Oct. 27, 2010, Office Action.
U.S. Appl. No. 12/114,091, Mail Date Dec. 17, 2010, Office Action.
U.S. Appl. No. 12/114,091, Mail Date Jul. 7, 2011, Office Action.

(56) References Cited

OTHER PUBLICATIONS

U.S. Appl. No. 12/114,091, Mail Date Apr. 5, 2012, Office Action.
U.S. Appl. No. 12/114,091, Mail Date Nov. 8, 2012, Office Action.
U.S. Appl. No. 12/122,603, Mail Date Mar. 3, 2011, Office Action.
U.S. Appl. No. 12/122,603, Mail Date Apr. 22, 2011, Office Action.
U.S. Appl. No. 12/122,603, Mail Date Sep. 23, 2011, Office Action.
U.S. Appl. No. 12/135,858, Mail Date Jul. 13, 2011, Office Action.
U.S. Appl. No. 12/135,858, Mail Date Feb. 16, 2012, Office Action.
U.S. Appl. No. 12/143,020, Mail Date May 11, 2011, Office Action.
U.S. Appl. No. 12/143,020, Mail Date Aug. 31, 2011, Office Action.
U.S. Appl. No. 12/143,020, Mail Date Feb. 23, 2012, Notice of Allowance.
U.S. Appl. No. 12/338,977, Mail Date Jan. 19, 2012, Office Action.
U.S. Appl. No. 12/338,977, Mail Date Jul. 11, 2012, Office Action.
U.S. Appl. No. 12/338,977, Mail Date Nov. 28, 2012, Office Action.
U.S. Appl. No. 12/338,977, Mail Date Sep. 29, 2011, Office Action.
U.S. Appl. No. 12/338,977, Mail Date Dec. 13, 2011, Office Action.
U.S. Appl. No. 12/338,977, Mail Date May 21, 2012, Office Action.
U.S. Appl. No. 12/402,398, Mail Date Mar. 9, 2010, Office Action.
U.S. Appl. No. 12/402,398, Mail Date May 20, 2010, Office Action.
U.S. Appl. No. 12/402,398, Mail Date Jan. 24, 2011, Office Action.
U.S. Appl. No. 12/402,398, Mail Date Sep. 20, 2012, Office Action.
U.S. Appl. No. 12/402,398, Mail Date Mar. 13, 2013, Notice of Allowance.
U.S. Appl. No. 12/403,256, Mail Date Dec. 16, 2009, Office Action.
U.S. Appl. No. 12/403,256, Mail Date Mar. 30, 2010, Office Action.
U.S. Appl. No. 12/403,256, Mail Date Aug. 19, 2010, Notice of Allowance.
U.S. Appl. No. 12/403,277, Mail Date Jul. 8, 2010, Office Action.
U.S. Appl. No. 12/403,277, Mail Date Oct. 12, 2010, Office Action.
U.S. Appl. No. 12/403,277, Mail Date Mar. 31, 2011, Office Action.
U.S. Appl. No. 12/403,277, Mail Date Apr. 3, 2012, Office Action.
U.S. Appl. No. 12/403,277, Mail Date Nov. 5, 2012, Office Action.
U.S. Appl. No. 12/481,377, Mail Date Apr. 28, 2011, Office Action.
U.S. Appl. No. 12/481,377, Mail Date Jun. 21, 2011, Office Action.
U.S. Appl. No. 12/481,377, Mail Date Jan. 3, 2012, Office Action.
U.S. Appl. No. 12/481,377, Mail Date Aug. 10, 2012, Notice of Allowance.
U.S. Appl. No. 12/548,274, Mail Date Dec. 28, 2011, Office Action.
U.S. Appl. No. 12/548,274, Mail Date Mar. 2, 2012, Office Action.
U.S. Appl. No. 12/548,274, Mail Date Sep. 10, 2012, Office Action.
U.S. Appl. No. 12/608,769, Mail Date Feb. 10, 2012, Office Action.
U.S. Appl. No. 12/608,769, Mail Date Aug. 22, 2012, Office Action.
U.S. Appl. No. 12/608,769, Mail Date Nov. 5, 2012, Notice of Allowance.
U.S. Appl. No. 12/608,773, Mail Date Jun. 7, 2012, Office Action.
U.S. Appl. No. 12/608,773, Mail Date Jul. 20, 2012, Office Action.
U.S. Appl. No. 12/608,773, Mail Date Jan. 7, 2013, Office Action.
U.S. Appl. No. 12/642,319, Mail Date Feb. 27, 2012, Office Action.
U.S. Appl. No. 12/642,319, Mail Date Aug. 28, 2012, Office Action.
U.S. Appl. No. 12/684,400, Mail Date Feb. 13, 2012, Office Action.
U.S. Appl. No. 12/684,400, Mail Date May 9, 2012, Office Action.
U.S. Appl. No. 12/684,400, Mail Date Oct. 16, 2012, Office Action.
U.S. Appl. No. 12/684,470, Mail Date Dec. 20, 2011, Office Action.
U.S. Appl. No. 12/684,470, Mail Date Mar. 23, 2012, Office Action.
U.S. Appl. No. 12/684,470, Mail Date Aug. 30, 2012, Office Action.
U.S. Appl. No. 12/684,542, Mail Date Jan. 30, 2012, Office Action.
U.S. Appl. No. 12/684,542, Mail Date Apr. 16, 2012, Office Action.
U.S. Appl. No. 12/684,542, Mail Date Sep. 13, 2012, Office Action.
U.S. Appl. No. 12/684,562, Mail Date Dec. 28, 2011, Office Action.
U.S. Appl. No. 12/684,562, Mail Date Feb. 16, 2012, Office Action.
U.S. Appl. No. 12/684,562, Mail Date Aug. 21, 2012, Office Action.
U.S. Appl. No. 12/684,569, Mail Date Dec. 20, 2011, Office Action.
U.S. Appl. No. 12/684,569, Mail Date Jan. 27, 2012, Office Action.
U.S. Appl. No. 12/684,569, Mail Date Jul. 30, 2012, Office Action.
U.S. Appl. No. 12/688,065, Mail Date Mar. 13, 2012, Office Action.
U.S. Appl. No. 12/688,065, Mail Date Apr. 26, 2012, Office Action.
U.S. Appl. No. 12/688,065, Mail Date Oct. 12, 2012, Office Action.
U.S. Appl. No. 12/724,304, Mail Date Feb. 10, 2012, Office Action.
U.S. Appl. No. 12/724,304, Mail Date Mar. 13, 2012, Interview Summary.
U.S. Appl. No. 12/724,304, Mail Date Jul. 11, 2012, Notice of Allowance.
U.S. Appl. No. 12/848,642, Mail Date Sep. 20, 2012, Office Action.
U.S. Appl. No. 12/848,642, Mail Date Nov. 9, 2012, Office Action.
U.S. Appl. No. 12/850,242, Mail Date Aug. 6, 2012, Office Action.
U.S. Appl. No. 12/850,242, Mail Date Oct. 17, 2012, Office Action.
U.S. Appl. No. 12/897,358, Mail Date Aug. 22, 2011, Office Action.
U.S. Appl. No. 12/897,358, Mail Date Jan. 12, 2012, Notice of Allowance.
U.S. Appl. No. 12/897,358, Mail Date Mar. 5, 2012, Notice of Allowance.
U.S. Appl. No. 12/941,809, Mail Date Dec. 13, 2011, Office Action.
U.S. Appl. No. 12/941,809, Mail Date Jan. 30, 2012, Office Action.
U.S. Appl. No. 12/941,809, Mail Date Jun. 1, 2012, Office Action.
U.S. Appl. No. 12/945,646, Mail Date Jan. 20, 2011, Office Action.
U.S. Appl. No. 12/945,646, Mail Date Jul. 6, 2011, Office Action.
U.S. Appl. No. 12/945,646, Mail Date Oct. 26, 2011, Office Action.
U.S. Appl. No. 12/945,646, Mail Date Feb. 21, 2012, Notice of Allowance.
U.S. Appl. No. 12/955,859, Mail Date May 26, 2011, Office Action.
U.S. Appl. No. 12/955,859, Mail Date Jul. 21, 2011, Office Action.
U.S. Appl. No. 12/955,859, Mail Date Dec. 15, 2011, Office Action.
U.S. Appl. No. 12/955,859, Mail Date Aug. 6, 2012, Office Action.
U.S. Appl. No. 12/961,331, Mail Date Dec. 4, 2012, Office Action.
U.S. Appl. No. 12/961,331, Mail Date Feb. 1, 2013, Office Action.
U.S. Appl. No. 12/966,923, Mail Date Feb. 3, 2012, Notice of Allowance.
U.S. Appl. No. 12/973,204, Mail Date Mar. 7, 2012, Notice of Allowance.
U.S. Appl. No. 12/987,792, Mail Date Mar. 13, 2012, Office Action.
U.S. Appl. No. 12/987,792, Mail Date Sep. 17, 2012, Office Action.
U.S. Appl. No. 13/026,989, Mail Date Sep. 16, 2011, Office Action.
U.S. Appl. No. 13/026,989, Mail Date Jun. 8, 2012, Office Action.
U.S. Appl. No. 13/028,041, Mail Date Jan. 4, 2013, Office Action.
U.S. Appl. No. 13/028,041, Mail Date Feb. 26, 2013, Office Action.
U.S. Appl. No. 13/030,922, Mail Date Dec. 18, 2012, Office Action.
U.S. Appl. No. 13/030,922, Mail Date Jan. 31, 2013, Office Action.
U.S. Appl. No. 13/039,087, Mail Date Jul. 17, 2012, Office Action.
U.S. Appl. No. 13/039,087, Mail Date Nov. 6, 2012, Notice of Allowance.
U.S. Appl. No. 13/111,371, Mail Date Oct. 12, 2012, Office Action.
U.S. Appl. No. 13/111,371, Mail Date Dec. 18, 2012, Office Action.
U.S. Appl. No. 13/153,594, Mail Date Jan. 29, 2013, Office Action.
U.S. Appl. No. 13/488,233, Mail Date Feb. 5, 2013, Notice of Allowance.
U.S. Appl. No. 13/490,143, Mail Date Jan. 4, 2013, Office Action.
U.S. Appl. No. 13/615,547, Mail Date Jan. 18, 2013, Office Action.
U.S. Appl. No. 29/296,370, Mail Date Aug. 18, 2008, Office Action.
U.S. Appl. No. 29/296,370, Mail Date Dec. 2, 2008, Notice of Allowance.
U.S. Appl. No. 29/296,370, Mail Date Apr. 1, 2009, Notice of Allowance.
U.S. Appl. No. 11/744,089, Mail Date Apr. 15, 2013, Office Action.
U.S. Appl. No. 13/112,618, Mail Date Mar. 29, 2013, Office Action.
U.S. Appl. No. 13/112,631, Mail Date Mar. 29, 2013, Office Action.
U.S. Appl. No. 13/308,227, Mail Date Apr. 10, 2013, Office Action.
U.S. Appl. No. 13/525,839, Mail Date Apr. 1, 2013, Office Action.
U.S. Appl. No. 13/615,547, Mail Date Apr. 12, 2013, Notice of Allowance.
U.S. Appl. No. 13/898,202, filed May 20, 2013, Walberg et al.
U.S. Appl. No. 10/786,444, Mail Date Jul. 11, 2013, Notice of Allowance.
U.S. Appl. No. 10/908,721, Mail Date Jul. 18, 2013, Notice of Allowance.
U.S. Appl. No. 11/396,141, Mail Date Aug. 21, 2013, Office Action.
U.S. Appl. No. 11/427,309, Mail Date Jun. 7, 2013, Notice of Allowance.
U.S. Appl. No. 11/532,325, Mail Date Jul. 17, 2013, Office Action.
U.S. Appl. No. 11/744,089, Mail Date Aug. 8, 2013, Notice of Allowance.
U.S. Appl. No. 12/106,928, Mail Date Jun. 28, 2013, Office Action.

(56) References Cited

OTHER PUBLICATIONS

U.S. Appl. No. 12/106,937, Mail Date Jun. 28, 2013, Office Action.
U.S. Appl. No. 12/338,977, Mail Date Jun. 19, 2013, Office Action.
U.S. Appl. No. 12/850,242, Mail Date Aug. 6, 2013, Notice of Allowance.
U.S. Appl. No. 12/941,809, Mail Date Jul. 3, 2013, Office Action.
U.S. Appl. No. 12/955,859, Mail Date Aug. 1, 2013, Notice of Allowance.
U.S. Appl. No. 12/961,331, Mail Date Jul. 3, 2013, Office Action.
U.S. Appl. No. 13/026,989, Mail Date Aug. 23, 2013, Office Action.
U.S. Appl. No. 13/030,922, Mail Date Jul. 18, 2013, Office Action.
U.S. Appl. No. 13/112,618, Mail Date Jun. 7, 2013, Office Action.
U.S. Appl. No. 13/112,631, Mail Date Jun. 26, 2013, Office Action.
U.S. Appl. No. 13/153,594, Mail Date May 29, 2013, Office Action.
U.S. Appl. No. 13/490,143, Mail Date Aug. 21, 2013, Issue Notification.
U.S. Appl. No. 13/525,839, Mail Date Jul. 15, 2013, Notice of Allowance.

* cited by examiner

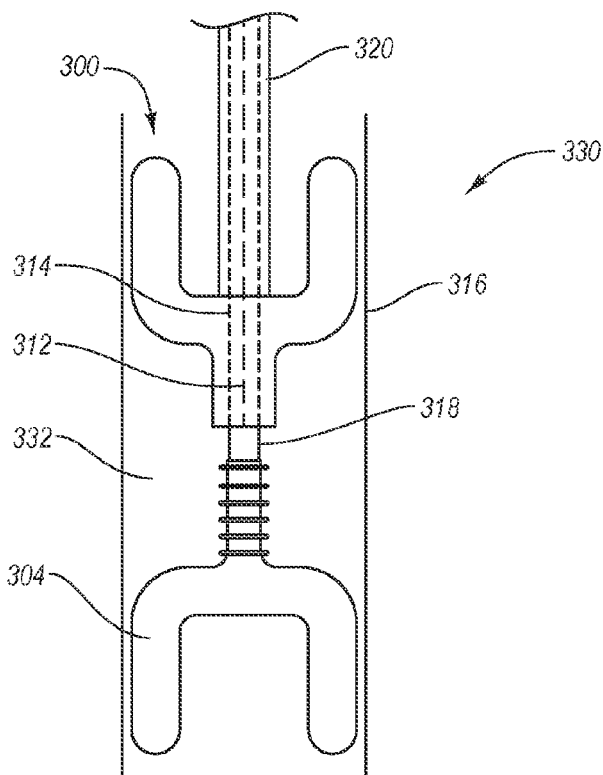
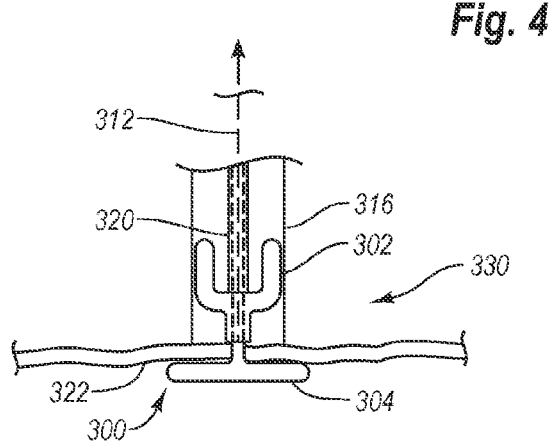
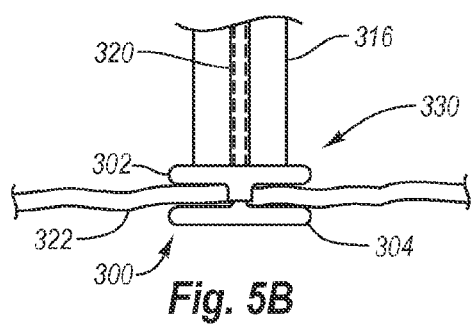

CLOSURE DEVICE

CROSS REFERENCE

This application is a continuation of U.S. patent application Ser. No. 12/608,769, filed on Oct. 29, 2009, now U.S. Pat. No. 8,398,676 which claims the benefit of, and priority to, U.S. Provisional Patent Application Ser. No. 61/109,822, filed on Oct. 30, 2008 and entitled "CLOSURE DEVICE," and Ser. No. 61/143,748, filed on Jan. 9, 2009 and entitled "CLOSURE DEVICE," all of which are incorporated in their entirety herein by this reference.

BACKGROUND

1. The Field of the Invention

The present disclosure relates generally to systems, devices, and methods for blocking an opening in body lumens. More particularly, the present disclosure relates to techniques for percutaneous closure of arterial and venous puncture sites, which are usually accessed through a tissue tract.

2. The Relevant Technology

A number of diagnostic and interventional vascular procedures are now performed transluminally. A catheter is introduced to the vascular system at a convenient access location and guided through the vascular system to a target location using established techniques. Such procedures require vascular access, which is usually established during the well-known Seldinger technique. Vascular access is generally provided through an introducer sheath, which is positioned to extend from outside the patient body into the vascular lumen. When vascular access is no longer required, the introducer sheath is removed and bleeding at the puncture site stopped.

One common approach for providing hemostasis (the cessation of bleeding) is to apply external force near and upstream from the puncture site, typically by manual compression. This approach suffers from a number of disadvantages. For example, the manual compression procedure is time consuming, frequently requiring one-half hour or more of compression before hemostasis is achieved. Additionally, such compression techniques rely on clot formation, which can be delayed until anticoagulants used in vascular therapy procedures (such as for heart attacks, stent deployment, non-optimal PTCA results, and the like) wear off. The anticoagulants may take two to four hours to wear off, thereby increasing the time required before completion of the manual compression procedure.

Further, the manual compression procedure is uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as twelve hours or more under close observation to assure continued hemostasis. During this time, renewed bleeding may occur, resulting in blood loss through the tract, hematoma and/or pseudo-aneurysm formation, as well as arteriovenous fistula formation. These complications may require blood transfusion and/or surgical intervention.

The incidence of complications from the manual compression procedure increases when the size of the introducer sheath grows larger, and/or when the patient is anticoagulated. The compression technique for arterial closure can be risky, and is expensive and onerous to the patient. Although the risk of complications can be reduced by using highly trained individuals, dedicating such personnel to this task is both expensive and inefficient. Nonetheless, as the number and efficacy of translumenally performed diagnostic and interventional vascular procedures increases, the number of patients requiring effective hemostasis for a vascular puncture continues to increase.

To overcome the problems associated with manual compression, the use of bioabsorbable sealing bodies is one example approach that has been proposed. Generally, this example approach relies on the placement of a thrombogenic and bioabsorbable material, such as collagen, at the superficial arterial wall over the puncture site. While potentially effective, this approach suffers from a number of problems. For example, bioabsorbable sealing bodies may lack a solid mechanical attachment of the sealing body to the tissue. Due to the lack of a solid mechanical attachment, the sealing body can wander within the tissue tract or move out of the puncture site, thus causing late bleeds. Conversely, if the sealing body wanders and intrudes too far into the arterial lumen, due to the lack of a solid mechanical attachment, intravascular clots and/or collagen pieces with thrombus attached can form and embolize downstream, causing vascular occlusion.

In addition to not having a solid mechanical attachment to the tissue, the sealing bodies may rely upon expandable materials to achieve hemostasis. Again, the expandable materials lack the security of a hard mechanical closure, thus potentially causing late bleeds and prolonging hemostasis.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Embodiments of the present disclosure provide systems, methods and devices for closing an opening in tissue. Embodiments of the disclosure can be configured to close an opening within a body lumen.

In one example embodiment, a device for closing an opening in a wall of a body lumen may include a closure element with a first flange and a second flange. Both the first flange and the second flange have a delivery cross-sectional dimension and a deployed cross-sectional dimension. The device further includes a first coupler element disposed on the first flange and a second coupler element disposed on the second flange, the first and second coupler elements cooperating to couple the first flange to the second flange.

In another example embodiment, a closure element for closing an opening in a body lumen includes a proximal flange with a first coupler element and a distal flange with a second coupler element. The closure element may also include a pull cord that is operatively associated with the distal flange such that the second coupler element may be coupled to the first coupler element by pulling the pull cord.

Another example embodiment includes a closure element that has a delivery configuration and a deployed configuration and is used to close an opening in a wall of a body lumen. The closure element includes a first flange with a delivery configuration and a deployed configuration such that the first flange can pass through the opening in the wall of the body lumen when in the delivery configuration, but not when in the deployed configuration. The closure element further includes a second flange having a delivery configuration and a deployed configuration, wherein the second flange cannot pass through the opening in the wall of the body lumen when in the deployed configuration. Moreover, the closure element may include a coupler portion positioned between the first flange and the second flange, the coupler portion having a cross-sectional dimension substantially equal to or smaller than the opening.

A further embodiment includes a system for closing an opening in a body lumen that includes a closure element, an actuator coupled to the closure element, and a handle assembly. The handle assembly may include a handle element operatively associated with a hub member such that the actuator moves the closure element from a delivery configuration to a deployed configuration upon rotation of the handle element.

Another embodiment of the invention includes a method of closing an opening in tissue that includes inserting a closure device into an opening formed in tissue. Applying a force to the actuator to change the closure element from a first configuration to a second configuration.

These and other advantages and features of the present disclosure will become more fully apparent from the following description and appended claims, or may be learned by the practice of the disclosure as set forth hereinafter.

BRIEF DESCRIPTION OF THE DRAWINGS

To further clarify the above and other advantages and features of the present disclosure, a more particular description will be rendered by reference to specific embodiments which are illustrated in the appended drawings. It is appreciated that these drawings depict only typical embodiments of the disclosure and are therefore not to be considered limiting of its scope. The embodiments will be described and explained with additional specificity and detail through the use of the accompanying drawings in which:

FIG. 4 is a partial cross-sectional view of a delivery system and the closure element of FIG. 1;

FIG. 5A is an illustration of the closure element of FIG. 1 partially deployed;

FIG. 5B is an illustration of the closure element of FIG. 1 fully deployed; and

DETAILED DESCRIPTION

In accordance with the present disclosure, there is provided closure devices configured to close an opening in tissue. The closure devices described herein may be formed of a bioabsorbable material or may be formed of a biocompatible material. It is further contemplated that the closure device may be coated with a covering membrane and/or another biocompatible coating as will be described in greater detail below. In one embodiment, the closure device may be configured to be received within and deployed from the lumen of a medical sheath, for example, a physician may utilize a 6 French sheath. However, it can be understood that embodiments of the closure device may be configured to be received within multiple sizes and configurations of sheaths and should not be limited to the example above and will accommodate newer and yet to be developed endoluminal techniques including venous techniques.

Figure 1:
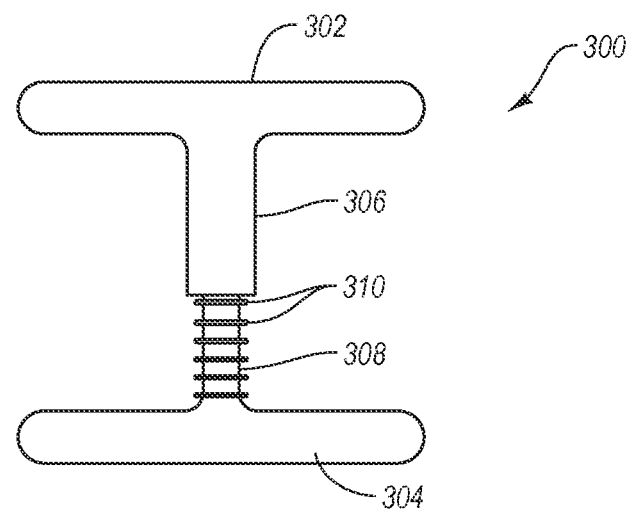
FIG. 1 illustrates an example embodiment of a closure element in accordance with the present disclosure.

Moving now to FIGS. 1 through 5B, an example closure device pursuant to embodiments of the present disclosure will be discussed. In particular, FIG. 1 illustrates an example closure element 300. The closure element 300 may include a proximal flange 302 and a distal flange 304. The proximal flange 302 may include a first coupler 306 while the distal flange 304 may include a second coupler 308. In at least one example embodiment, the second coupler 308 may include friction elements 310, as illustrated in FIG. 1. In further embodiments, the first coupler 306 and second coupler 308 may be configured to couple together in any of a variety of configurations, such as by friction, threading, snap-fit, tongue-and-groove, similar coupling configurations, or combinations thereof. In a yet further embodiment, once the second coupler 308 is inserted into the first coupler 306, a pin or other elongate member may be inserted through the second coupler 308 to force the second coupler 308 outward and into more secure contact with the first coupler 306.

Briefly, in operation, the closure element 300 may be inserted into an opening in a body lumen in a delivery configuration. The distal flange 304 may then be deployed within the body lumen and the proximal flange 302 may be deployed outside the body lumen. The proximal flange 302 and the distal flange 304 may then be coupled or otherwise joined together through the opening in the body lumen. In one example, the second coupler 308 is pressed into the first coupler 306 and locked into place with friction elements 310 that allow the second coupler 308 to be pressed into the first coupler 306 but do not allow the second coupler 308 to be released from the first coupler 306.

The closure element 300, illustrated in FIG. 1, may have various characteristics and configurations. For example, one way in which the closure element 300 may vary is the type of material used to make the closure element 300. In one embodiment the closure element 300 may be manufactured from a bioabsorbable, bioresorbable, bioerodible, or biodegradable material. Examples of suitable materials for use are metals, metal alloys, polymers, or combinations thereof that decompose or biodegrade in a biological environment such as within a body lumen. For example, and not by limitation, suitable bioabsorbable materials may include magnesium, zinc, iron, silicon, zinc titanium, magnesium lithium, of colic acid (PGA), polyhydroxybutyric acid, polyL-Lactic acid (PLLA), poly dl-lactic acid (PDLLA), polydilactidel glycolide acid, polydilactid acid, PolyDL Lactide-co-gycolide, Polylactic acid, Polyhydroxyalkanoates, polylactic acid-co-caprolactone, polylactic acid-co-Chitosan, poly-phosphazenes, poly-anhydrides, degradable poly-urethanes, biodegradable poly-carbonates, biodegradable ceramics such as those based on tricalcium phosphate or hydroxyapatite, analogous materials, co-polymers thereof, derivatives thereof, and any combinations thereof.

In addition to the various types of materials that may be used to manufacture the closure element 300, the closure element 300 may include additional material properties that may be useful. For example, the closure element 300 may be covered with a flexible membrane to aid in sealing the opening. The flexible membrane may be formed of a flexible bio-compatible or bioabsorbable material such as any of those that are described above. Moreover, the closure element 300 may further include a beneficial agent either disposed thereon as a coating or integrally formed within the material of the closure element 300. The beneficial agent may be configured to aid in healing and/or reduce the potential for infection.

Moreover, the closure element 300 may include additional elements to help a user place the closure element 300 within a body lumen. For example, the closure component 300 may further include a radiopaque marker or radiopaque coating in order to aid the user in positioning the closure element 100 within the puncture site of the body lumen. The radiopaque marker may be formed within the wall of the body of the first or second flange 302, 304 in the form of a rivet. In a further embodiment, a radiopaque coating may be disposed on the closure element 300 as a thin coating of radiopaque metal such as gold, tantalum, platinum, iridium, similar metals, or combinations thereof. In a yet further embodiment, the radiopaque coating may comprise an iodine contained polymer such as polytyrosine carbonate with iodine.

In addition to material aspects of the closure element 300, the configuration of the closure device 300 may vary from one embodiment to the next. For example, the cross-sectional configuration of the proximal and distal flanges 302 and 304 may vary from one embodiment to the next. In one example embodiment, the proximal and distal flanges 302 and 304 may have a substantially circular or disc-like shape/configuration, as illustrated in FIG. 1. In other examples, the proximal and distal flanges 302 and 304 may have various other shapes or configurations, such as square, rectangular, oval, or any other cross-sectional configuration. Moreover, the proximal flange 302 and the distal flange 304 may have differing shapes or configurations. In a yet further embodiment, the proximal flange 302 and the distal flange 304 may be rotationally offset with respect to each other.

Just as the shape and configuration of the proximal flange 302 and the distal flange 304 may vary, so too may the cross-sectional profile vary from one embodiment to the next. As illustrated in FIG. 1, the proximal flange 302 and the distal flange 304 have a T-shaped cross-sectional profile with a substantially flat horizontal cross-bar section. In other example embodiments, the cross-bar section may further include ridges or protrusions that may be used to grip tissue and further anchor the closure element 300 within an opening in a body lumen.

Moreover, the second coupler 308 and first coupler 306 may have any configuration for joining or coupling the proximal flange 302 and the distal flange 304 together. For example, in one embodiment, the first coupler 306 and second coupler 308 may couple together through a hook and anchor configuration. In a further embodiment, the first coupler 306 and second coupler 308 may have corresponding internal and external threads and may screw together. In a yet further embodiment, the first coupler 306 and second coupler 308 may have any other configuration that could be used to join or couple the proximal flange 302 to the distal flange 304. Moreover, in other example embodiments, the proximal flange 302 and the distal flange 304 may be made from the same piece of material or permanently joined together prior to deployment.

Figure 2:
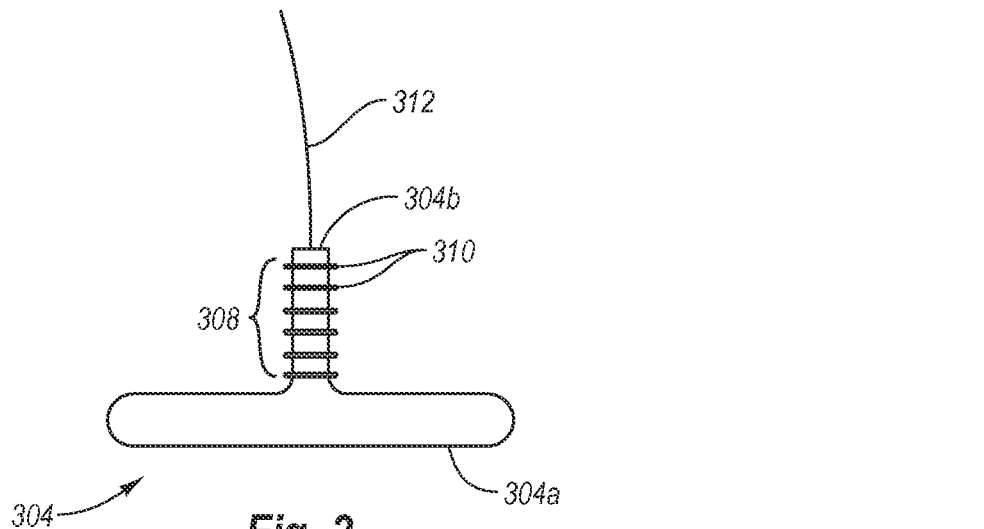
FIGS. 2 and 3 illustrate example components of an example embodiment of the closure element of FIG. 1.

FIG. 2 illustrates an isolated view of an example distal flange 304. As illustrated in FIG. 2, the distal flange 304 may have a distal end 304A and a proximal end 304B. Moreover, the distal flange 304 may include a second coupler 308 with a plurality of friction elements 310 located on the second coupler 308. In one example embodiment, the distal flange 304 may further include a pull cord 312. The distal flange 304 may vary from one embodiment to the next. For example, the friction elements 310 may vary from one embodiment to the next. In one example embodiment, illustrated in FIG. 2, the friction elements 310 may be equally spaced and arranged on the second coupler 308. In a further example embodiment, the friction elements 310 may be randomly arranged. Moreover, in other embodiments, there may be only one friction element 310 instead of a plurality of friction elements 310.

Another way in which the friction elements 310 may vary is the type of friction elements 310 used. For example, the friction elements 310 in one example embodiment may be o-ring type structures that are configured to have a tolerance fit with the first coupler 306 of the proximal flange 302. In another example, the friction elements 310 may include teeth or ramps which could be complimentary to teeth or ramps disposed within the first coupler 306, thereby, causing the proximal flange 302 and the distal flange 304 to be locked together.

Figure 3:
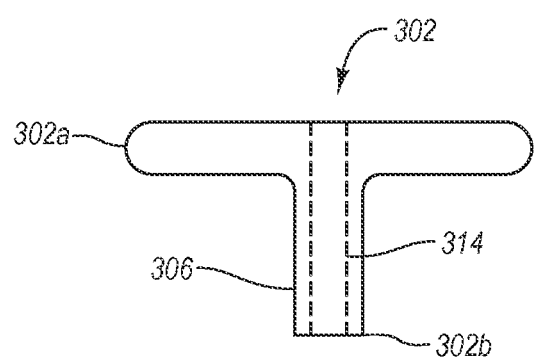

FIG. 3 illustrates an isolated view of an example of the proximal flange 302. The proximal flange 302 may include a proximal end 302a, a distal end 302b and a first coupler 306 that includes a passage 314. The proximal flange 302 may vary from one embodiment to the next. For example, the passage 314 in the first coupler 306 may vary. As illustrated in FIG. 3, the passage 314 may have a constant cross-sectional dimension. In other example embodiments, the cross-sectional dimension of the passage 314 may vary. For example, the cross-sectional dimension may become smaller moving from the distal end 302b to the proximal end 302a of the proximal flange 302. In this way, the second coupler 308 on the distal flange 304 may be configured to wedge or otherwise interface with the narrowing passage 314.

The material of the proximal flange 302 and the distal flange 304 may vary from one embodiment to the next. The proximal flange 302 and the distal flange 304 may be generally constructed of a flexible biocompatible material, such as a bioabsorbable material. Examples of suitable materials are described in more detail above.

FIGS. 4 through 5B illustrate example embodiments of a closure device 330 that employs the closure element 300. As shown in FIG. 4, the proximal flange 302 and the distal flange 304 may be configured such that they are able to collapse, bend, or flex at approximately right angles with respect to the first coupler 306 and second coupler 308 respectively, thus forming a delivery configuration. While in the delivery configuration, the proximal flange 302 and the distal flange 304 may be inserted within a delivery tube 316. The delivery tube 316 may have a passage 332 that has a cross-sectional dimension that allows the proximal flange 302 and the distal flange 304 to be inserted within the passage 332. Moreover, the closure device may include a first pusher 318 and a second pusher 320, with the first pusher 318 operatively associated with the distal flange 304, and the second pusher 320 operatively associated with the proximal flange 302.

The configuration of the closure device 330 may vary from one embodiment to the next. For example, and as illustrated in FIG. 4, the first pusher 318 may be configured to extend through the passage 314 of the proximal flange 302 and interface with or otherwise apply a force to the distal flange 304. The second pusher 320 may be configured with a larger cross-sectional dimension such that it cannot pass through the passage 314 of the proximal flange 302, and thus, the second pusher 320 can interface with or otherwise apply a force to the proximal flange 302.

While positioned within the delivery tube 316, the proximal flange 302 and the distal flange 304 may be uncoupled together. When the proximal and distal flanges 302 and 304 are not connected, the first and second pushers 318 and 320 can move the proximal flange 302 and distal flange 304 independent from one another to advance or retract the proximal flange 302 and/or distal flange 304. In further embodiments, the proximal flange 302 and the distal flange 304 may be coupled together during the delivery of the closure element 300 within the opening in the body lumen. When the proximal and distal flanges are coupled together while in the delivery tube 316, a single pusher may be used and there may not be a need for a first and second pusher. For example, the second pusher 320 alone may move and control both the proximal and distal flanges 302 and 304.

FIGS. 5A and 5B illustrate an example implementation of the closure device 330. In particular, FIG. 5A illustrates the deployed configuration of the distal flange 304 within the body lumen. In order to deploy the distal flange 304, delivery tube 316 is inserted into an opening located in the body lumen wall 322. At that point, the first pusher 318 may apply a force in the distal direction on the distal flange 304. Once the distal flange 304 leaves or exits the delivery tube 316, the distal flange 304 may elastically or otherwise move from the u-shape configuration or delivery configuration into a deployed configuration, as shown in FIG. 5A.

Once deployed, the distal flange 304 may then be attached or coupled to the proximal flange 302, if not already coupled. In one example embodiment, this attachment may occur by way of the pull-cord 312. For example, a user of the closure device 330 may pull the pull-cord 312 in a proximal direction, thus pulling the distal flange 304 relative to and towards the proximal flange 302. In this way, the second coupler 308 located on the distal flange 304 may be pulled into the first coupler 306 located on the proximal flange 302. In further embodiments, the deployment of the closure element 300 could still move forward at this point without having connected the proximal flange 302 to the distal flange 304. In further embodiments, the pull-cord 312 can be coupled to an automated and/or powered tensioning device configured to provide a desired tension to the pull-cord 312. In yet further embodiments, the pull-cord 312 may be sufficiently rigid to transfer both distal and proximal forces to the closure element 300. In additional embodiments, the closure element 300 and any components thereof may be coupled to a closure system configured to deploy the closure element 300 upon manipulation of the closure system by a user.

The spacing between the proximal flange 302 and distal flange 304 is adjustable depending upon the amount of force applied to the distal flange 304 by the pull-cord 312 and depending on the thickness of the body lumen wall where the closure element 300 is being deployed, thereby enabling the closure element 300 to be adjusted for various anatomies. As will be described in greater detail below, a charge of hemostatic material may be disposed proximal to the deployed closure element 300, such as within the tissue tract and/or against the outer surface of the deployed proximal flange 302 and body lumen, to further enhance sealing.

Moving now to FIG. 5B, the proximal flange 302 is shown in a deployed configuration outside of the delivery tube 316. In order for the proximal flange 302 to achieve the deployed configuration, the second pusher 320 may apply a force in the distal direction upon the proximal flange 302. While the second pusher 320 applies a force in the distal direction on the proximal flange 302, the delivery tube 316 may be pulled in the proximal direction such that the proximal flange 302 exits the delivery tube 316. Upon exiting the delivery tube 316, the proximal flange 302 may move elastically or otherwise from the delivery configuration to the deployed configuration such that the proximal flange 302 extends outward.

If the proximal flange 302 and the distal flange 304 have not yet been coupled together at this point, then the proximal flange 302 and the distal closure element may be pressed together such that the second coupler 308 located on the distal flange 304 may be pressed into the first coupler 306 located on the proximal flange 302. This may be done by use of a pull-cord 312, the first pusher 318, and/or second pusher 320, as discussed above. Once the proximal flange 302 and the distal flange 304 are coupled together and surround the lumen wall 322, the delivery tube 316 along with the first pusher 318 and second pusher 320 may be removed from the patient, while the closure element 300 remains to at least partially occlude or block the opening in the body lumen wall 322.

The closure device discussed with the various example embodiments of the present invention may include various other configurations. For example, any configuration of the closure device that includes a closure element that is able to anchor on the inside surface of the body lumen wall as well as on the outside surface of the body lumen wall (i.e. sandwich the wall of the body lumen between two portions of the closure element) may be used with the closure device.

As briefly mentioned above, the closure device 330 may include a hemostatic agent. For example, the passage 332 may be at least partially filled with the hemostatic agent in the space between the proximal flange 302 and the distal flange 304 such that as the closure element 300 is deployed, the hemostatic agent may be deployed proximate the opening in the tissue.

The hemostatic agent may be any material that is known to aid in the healing of the body lumen wall as well as to cause the cessation of bleeding. Moreover, the hemostatic agent may contain any material or agent that may be used to avoid infection. Suitable hemostatic materials for any of the embodiments described above may include chitosan, collagen, thrombin, PEG or other biocompatible materials. In one embodiment, chitosan may be utilized. The chitosan hemostatic composition can provide a strong clotting action to seal a hole, puncture, incision, or any other bleeding site to promote enhanced healing of the bleeding site and reduce opportunities for infection. Additionally, the chitosan hemostatic composition can be configured to swell in the presence of blood to form a hemostatic barrier that covers or otherwise plugs the bleeding site and/or aids the hemostasis of the percutaneous tissue tract.

Chitosan is a polycationic polymer derived from chitin, which can also be used as described herein. Chitosan has a positive charge from primary amine groups that can interact with the negative charge of the lipids present on cell surfaces, such as blood cells. This electrostatic interaction has been identified as an aspect of the hemostatic properties of chitosan. Dry chitosan compositions can have increased hemostatic properties by increasing surface area, and thereby the contact area with blood. Processing methods, such as freeze drying, puffing, foaming, sponging, ballooning, combinations thereof, or the like, can be used to provide a porous, open cellular, or closed cellular structure with increased surface area. In addition to chitosan and/or chitin, other polymers having N-acetylglucosamines and N-glucosamines, such as poly-beta-1→4-N-acetylglucosamines with or without one or more monosaccharides being deacetylated and poly-beta-1→4-N-glucosamines, and derivatives thereof.

The chitosan or other similar polymer used in various embodiments of the present invention may be purified to facilitate use in a medical device and or used within the body of a subject. This may include being purified to remove proteins or other organic and/or inorganic contaminants. Such purification and processing of chitosan is well known in the art. Accordingly, the chitosan or other similar polymer can be considered to be biocompatible, immunoneutral, and/or generally recognized as safe for use with or within a subject, such as a human or other animal.

Accordingly, the previous figures and the corresponding text provide a number of different components and systems that may be used to close an opening in a body lumen. In addition to the foregoing, other example embodiments may also be described in terms of flowcharts comprising one or more acts in a method for accomplishing a particular result.

Figure 6:
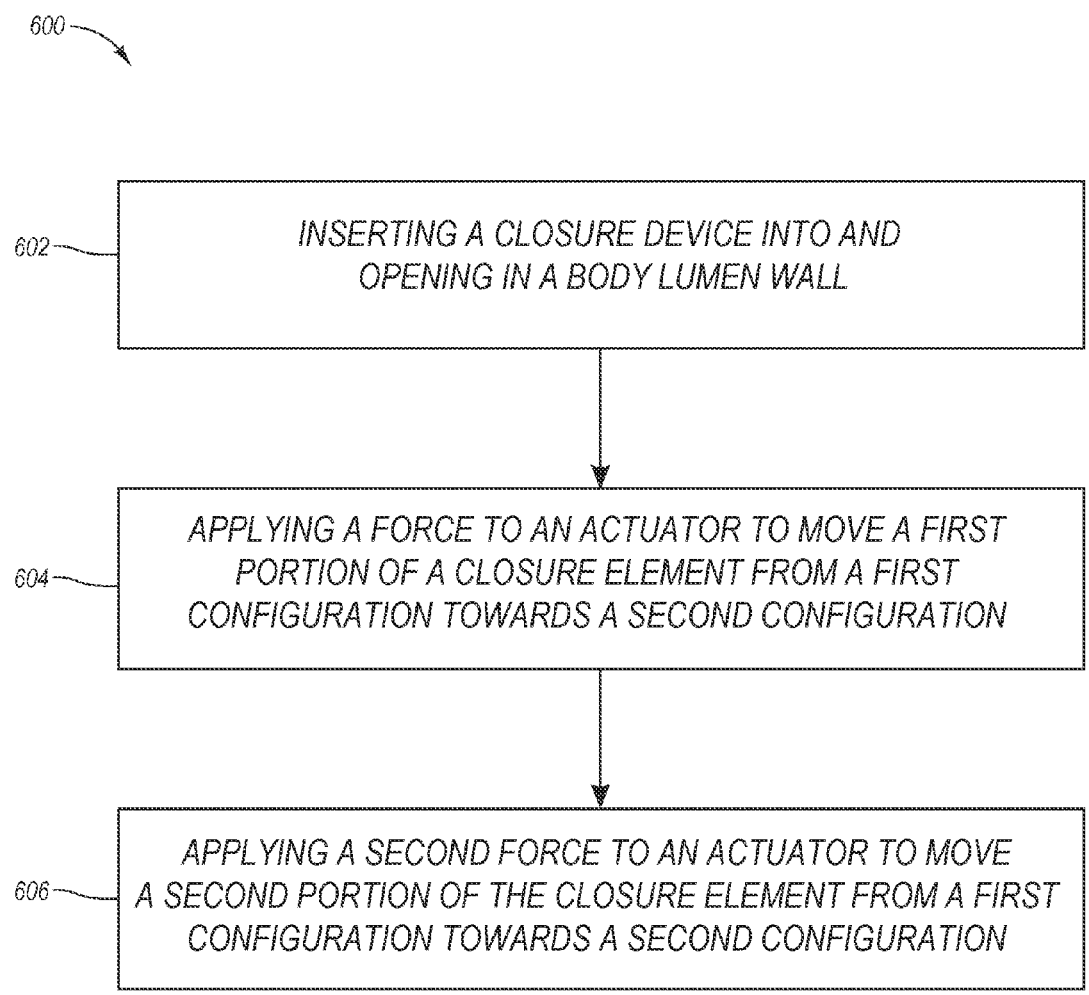
FIG. 6 is a flow chart showing an example method of closing an opening in tissue in accordance with the present disclosure.

For example, FIG. 6 illustrates a method 600 of closing an opening in tissue. The acts of method 600 are discussed more fully below with respect to the disclosures of FIGS. 1-5.

For example, FIG. 6 shows that a method in accordance with an example implementation of the invention may include inserting 602 a closure device into an opening in a body lumen wall. Inserting a closure device may involve inserting a closure device into an opening formed in tissue, the closure device including a delivery tube, an actuator, and a closure element, the closure element defined by a body having a proximal portion, a distal portion and a waist. For example, as shown in FIG. 5A, the closure element 300 may be inserted through the proximal lumen wall 322 or through an introducer that has already been implanted/positioned through the lumen wall.

After the closure device is inserted into an opening, a force may be applied 604 to the actuator to move a first portion of a closure element from a first configuration to a second configuration. Applying a force may involve applying a force to the actuator to move the distal portion of the closure element from a first configuration toward a second configuration, wherein in the second configuration, portions of the closure element protrude from the body. For example, as shown in FIG. 5A, the pull cord 312 may be moved in a proximal direction (as indicated by the arrow), thus causing the distal flange 304 to change from a delivery configuration to a deployed configuration.

Next, a second force may be applied 606 to an actuator to move a second portion of the closure element from a first configuration towards a second configuration. Applying a second force may involve applying a second force to the actuator to move the proximal portion of the closure element from a first configuration toward a second configuration. For example, and as illustrated in FIG. 5B, the actuator second pusher 320 may be moved in a distal direction, thus causing the proximal flange 302 to change from a delivery configuration to a deployed configuration.

After the closure element is fully deployed, the closure device may be disengaged from the closure element and removed from the patient.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope. It shall be further understood that although the present disclosure has been described in relation to vessel closure, it is contemplated that the closure component of the present invention may be utilized to close other openings in the body such as PFO openings, or openings formed in organs such as the stomach for certain surgical procedures, and/or for closing fistulae.

What is claimed is:

1. A method of closing an opening in tissue, comprising:
    inserting a closure device at least partially through an opening formed in tissue, the closure device including a delivery tube, an actuator, and a closure element, the closure element having a delivery configuration and a deployed configuration, the closure element comprising:
        a first flange configured to move between the delivery configuration and the deployed configuration, the first flange having a delivery cross-sectional dimension in the delivery configuration and a deployed cross-sectional dimension in the deployed configuration;
        a second flange configured to move between the delivery configuration and the deployed configuration, the second flange having a delivery cross-sectional dimension in the delivery configuration and a deployed cross-sectional dimension in the deployed configuration;
        a first coupler element disposed on the first flange extending in a first direction; and
        a second coupler element disposed on the second flange extending in a second direction, the first direction and the second directions being parallel but opposite, the first flange extending in the second direction in its delivery configuration and the second flange extending in the first direction in its delivery configuration, the first coupler element and the second coupler element configured to couple the first flange to the second flange, the first coupler element and the second coupler element being uncoupled in the delivery configuration, wherein the first coupler element further includes friction elements that resist relative movement between the first coupler element and the second coupler element,
    wherein the first and second flanges are positioned simultaneously in the delivery tube in the delivery configuration, and
    wherein the delivery cross-sectional dimension of the first flange is smaller than the deployed cross-sectional dimension of the first flange, the delivery cross-sectional dimension of the second flange is smaller than the deployed cross-sectional dimension of the second flange, and the delivery cross-sectional dimension of the second flange is smaller than the deployed cross-sectional dimension of the second flange,
    applying a force to the actuator to move the first flange of the closure element from the delivery configuration toward the deployed configuration;
    applying a second force to the actuator to move the second flange of the closure element from the delivery configuration toward the deployed configuration; and
    applying a third force to the actuator to couple the first flange to the second flange.

2. The method recited in claim 1, further comprising engaging the first flange of the closure element with a distal surface of tissue adjacent the opening when the first flange of the closure element is in the deployed configuration and prior to moving the second flange from the delivery a configuration toward the deployed configuration.

3. The method according to claim 1, further comprising deploying a hemostatic material on or adjacent to the opening in the tissue.

4. The method recited in claim 1, further comprising disengaging the delivery tube and actuator from the closure element and removing the delivery tube and actuator from the opening in the tissue.

5. The method of claim 1, wherein applying the third force to the actuator to couple the distal portion to the proximal portion includes pressing the second coupler element of the second flange over the first coupler element of the distal element.

6. A method of closing an opening in tissue, comprising:
    inserting a closure device at least partially through an opening formed in tissue, the closure device including a delivery tube, an actuator, and a closure element, the closure element defined by a body having a proximal portion having a first flange, a distal portion having a second flange, and a waist, the closure element further comprising a first coupler element disposed on the first flange extending in a first direction and a second coupler element disposed on the second flange extending in a second direction, the first direction and the second directions being parallel but opposite, the first flange extending in the second direction in its delivery configuration and the second flange extending in the first direction in its delivery configuration, the first coupler element and the second coupler element configured to couple the first flange to the second flange, the first coupler element and the second coupler element being uncoupled in the delivery configuration, wherein the first coupler element further includes friction elements that resist relative movement between the first coupler element and the second coupler element, wherein the first and second flanges are positioned simultaneously in the delivery tube in the delivery configuration, and wherein the delivery cross-sectional dimension of the first flange is smaller than the deployed cross-sectional dimension of the first flange, the delivery cross-sectional dimension of the second flange is smaller than the deployed cross-sectional dimension of the second flange, and the delivery cross-sectional dimension of the second flange is smaller than the deployed cross-sectional dimension of the second flange;

applying a force to the actuator to move the first flange of the closure element from the delivery configuration toward a deployed configuration by pushing the first flange out of the delivery tube and into the opening formed in the tissue, while maintaining the second flange of the closure device in the delivery configuration;

applying a second force to the actuator to move the second flange of the closure element from the delivery configuration toward the deployed configuration; and applying a third force to the actuator to couple the first flange to the second flange.

7. The method of claim 6, wherein applying the third force to the actuator to couple the first flange to the second flange includes pressing a waist portion of one of the first flange or the second flange into a waist portion of the opposite portion.

8. The method recited in claim 6, further comprising engaging the first flange of the closure element with a distal surface of tissue adjacent the opening when the first flange of the closure element is in the deployed configuration and prior to moving the second flange from the delivery configuration toward the deployed configuration.

9. The method according to claim 6, further comprising deploying a hemostatic material on or adjacent to the opening in the tissue.

10. The method recited in claim 6, further comprising disengaging the delivery tube and actuator from the closure element and removing the delivery tube and actuator from the opening in the tissue.

11. A method of closing an opening in tissue, comprising:
inserting a closure device at least partially through an opening formed in tissue, the closure device including a delivery tube, an actuator, and a closure element, the closure element defined by a body having a distal portion, a proximal portion, and a waist, the closure element comprising:
the distal portion being configured to move between a delivery configuration and a deployed configuration, the distal portion having a delivery cross-sectional dimension in the delivery configuration and a deployed cross-sectional dimension in the deployed configuration;
the proximal portion being configured to move between a delivery configuration and a deployed configuration, the proximal portion having a delivery cross-sectional dimension in the delivery configuration and a deployed cross-sectional dimension in the deployed configuration;
a first coupler element disposed on the distal portion extending in a first direction; and
a second coupler element disposed on the proximal portion extending in a second direction, the first direction and the second directions being parallel but opposite, the distal portion extending in the second direction in its delivery configuration and the proximal portion extending in the first direction in its delivery configuration, the first coupler element and the second coupler element configured to couple the distal portion to the proximal portion, the first coupler element and the second coupler element being uncoupled in the delivery configuration, wherein the first coupler element further includes friction elements that resist relative movement between the first coupler element and the second coupler element,
wherein the delivery cross-sectional dimension of the distal portion is smaller than the deployed cross-sectional dimension of the distal portion, and the delivery cross-sectional dimension of the proximal portion is smaller than the deployed cross-sectional dimension of the proximal portion,
applying a force to the actuator to move the distal portion of the closure element from a pre-deployed configuration to a deployed configuration by pushing the distal portion out of the delivery tube and into the opening formed in the tissue, while maintaining the proximal portion of the closure device in a pre-deployed configuration, wherein in the deployed configuration, a flange of the distal portion protrudes outward from the body;
applying a second force to the actuator to move the proximal portion of the closure element from the pre-deployed configuration to a deployed configuration by pushing the proximal portion out of the delivery tube and into the opening formed in the tissue, wherein in the deployed configuration, a flange of the proximal portion protrudes outward from the body.

12. The method recited in claim 11, further comprising engaging the distal portion of closure element with a distal surface of tissue adjacent the opening when the distal portion of the closure element is in the second configuration and prior to moving the proximal portion from a first configuration toward a second configuration.

13. The method according to claim 11, further comprising deploying a hemostatic material on or adjacent to the opening in the tissue.

14. The method recited in claim 11, further comprising disengaging the delivery tube and actuator from the closure element and removing the delivery tube and actuator from the opening in the tissue.

* * * * *